US005658739A

United States Patent [19]

Woods, Jr.

[11] Patent Number: 5,658,739
[45] Date of Patent: Aug. 19, 1997

[54] METHOD FOR CHARACTERIZATION OF THE FINE STRUCTURE OF PROTEIN BINDING SITES

[75] Inventor: Virgil L. Woods, Jr., San Diego, Calif.

[73] Assignee: The Regents of the University of California, Oakland, Calif.

[21] Appl. No.: 240,593

[22] Filed: May 10, 1994

[51] Int. Cl.$^6$ .................. G01N 33/53; G01N 30/02; G01N 30/72; C12Q 1/37
[52] U.S. Cl. .................. 435/7.1; 435/23; 435/24; 436/501; 436/536; 436/57; 436/86; 436/89; 436/161; 436/173; 436/174; 436/175
[58] Field of Search .................. 435/7.1, 23, 24; 436/501, 536, 57, 86, 89, 161, 173, 174, 175

[56] References Cited

U.S. PATENT DOCUMENTS

| | | | |
|---|---|---|---|
| 3,560,158 | 2/1971 | Benson | 436/57 |
| 3,623,840 | 11/1971 | Benson | 436/57 |
| 3,828,102 | 8/1974 | Fromageot et al. | 436/545 |
| 4,153,416 | 5/1979 | Bonner et al. | 436/57 |
| 4,517,686 | 5/1985 | Ruoslahti et al. | 623/1 |
| 4,578,079 | 3/1986 | Ruoslahti et al. | 623/11 |
| 4,589,881 | 5/1986 | Pierschbacher et al. | 623/11 |
| 4,614,517 | 9/1986 | Ruoslahti et al. | 530/330 |
| 4,661,111 | 4/1987 | Ruoslahti et al. | 623/11 |
| 4,792,525 | 12/1988 | Ruoslahti et al. | 435/240.243 |
| 4,956,303 | 9/1990 | Self | 436/542 |
| 4,963,263 | 10/1990 | Kauvar | 210/635 |
| 5,030,565 | 7/1991 | Niman et al. | 530/387.7 |

OTHER PUBLICATIONS

Arnon et al, *Structural Basis of Antigenic Specificity and Design of New Vaccines*, FASEB, vol. 6, pp. 3265–3274, Nov. 1992.

Bai et al, *Primary Structure Effects on Peptide Group Hydrogen Exchange*, PROTEINS: Structure, Function, and Genetics, vol. 17, pp. 75–86, 1993.

Beasty et al, *Characterization of an Early Intermediate in the Folding of the β Subunit of Tryptophan Synthase by Hydrogen Exchange Measurement*, Biochemistry, vol. 24, pp. 3547–3553, 1985.

Benjamin et al, *Long–Range Changes in a Protein Antigen Due to Antigen–Antibody Interaction*, Biochemistry, vol. 31, pp. 9539–9545, 1992.

Breddam, *Serine Carboxpeptidases. A Review.*, Carlsberg Res. Commun, vol. 51, pp. 83–128, 1986.

Burns et al, *Selective Reduction of Disulfides by Tris(2–Carboxyethyl)Phosphine*, J. Org. Chem., vol. 56, pp. 2648–2650, 1991.

Burz et al, *Mapping Structural Perturbations in Escherichia Coli Aspartate Transcarbamylase by Medium Resolution Hydrogen Exchange*, Biophys. J., vol. 49, pp. 70–72, Jan. 1986.

Byrne et al, *An Improved Freeze–Drying Technique for the Study of Hydrogen Exchange of Proteins and Poly–peptides*, Analytical Biochemistry, vol. 33, pp. 414–428, 1970.

Chi et al, *Use of Deuterium–Hydrogen Exchange to Characterize the Fragmentation Pathways of Arteether and its Metabolites in a Thermospray Mass Spectrometer*, Organic Mass Spectrometry, vol. 28, 12–17, 1993.

Connelly et al, *Isotope Effects in Peptide Group Hydrogen Exchange*, Proteins: Structure, Function, and Genetics, vol. 17, pp. 87–92, 1993.

Englander et al, *Hydrogen Exchange Studies of Respiratory Proteins*, The Journal of Biological Chemistry, vol. 248, No. 13, pp. 4852–4861, Jul. 10, 1973.

Englander et al, *Hydrogen–Tritium Exchange*, Methods in Enzymology, vol. 26, pp. 406–413, 1972.

Englander et al, *Hydrogen–Tritium Exchange*, Methods in Enzymology, vol. 49, pp. 24–39, 1978.

Englander et al, *Hydrogen–Tritium Exchange of the Random Chain Polypeptide*, Biopolymers, vol. 7, pp. 379–393, 1969.

Englander et al, *Hydrogen–Tritium Exchange Survey of Allosteric Effects in Hemoglobin*, Biochemistry, vol. 26, pp. 1846–1850, 1987.

Englander et al, *Individual Breathing Reactions Measured in Hemoglobin by Hydrogen Exchange Methods*, Biophys. J., vol. 10, pp. 577–589, 1979.

Englander et al, *Protein Hydrogen Exchange Studied by the Fragment Separation Method*, Analytical Bio–Chemistry, vol. 147, 234–244 1985.

Fesik et al, *Amide Proton Exchange Rates of a Bound Pepsin Inhibitor Determined by Isotope–Edited Proton NMR Experiments*, Biochemical and Biophysical Research Communications, vol. 147, No. 3, pp. 892–898, Sep. 30, 1987.

Fusek et al, *Enzymic Properties of Thermopsin*, The Journal of Biological Chemistry, vol. 265, No. 3, pp. 1496–1501, Jan. 25, 1990.

Gray, *Disulfide Structures of Highly Bridged Peptides: A New Strategy for Analysis*, Protein Science, vol. 2, pp. 1732–1748, 1993.

Gray, *Echistatin Disulfide Bridges: Selective Reduction and Linkage Assignment*, Protein Science, vol. 2, pp. 1749–1755, 1993.

Hartman et al, *Examination of the Function of Active Site Lysine 329 of Ribulose–Bisphosphate Carboxylase/Oxygenase as Revealed by the Proton Exchange Reaction*, The Journal of Biological Chemistry, vol. 246, No. 20, pp. 11784–11789, Jul. 15, 1989.

Hommel et al, *Structure–Function Relationships in Human Epidermal Growth Factor Studied by Site–Directed Mutagenesis and H NMR*, Biochemistry, vol. 30, pp. 8891–8898, 1991.

Horsfall et al, *Eptitope Mapping*, Immunology Today, vol. 12, No. 7, pp. 211–213, 1991.

(List continued on next page.)

*Primary Examiner*—Lora M. Green
*Attorney, Agent, or Firm*—Poms, Smith, Lande & Rose

[57] ABSTRACT

The binding sites of binding proteins and their binding partners are characterized, at the individual amino acid level, by a combination of tritium exchange labeling and sequential degradation and analysis of tritiated fragments under slowed exchange conditions.

15 Claims, 10 Drawing Sheets

OTHER PUBLICATIONS

Katta et al, *Hydrogen/Deuteruim Exchange Electrospray Ionization Mass Spectrometry: A Method for Probing Protein Conformational Changes in Solution*, J. Am. Chem. Soc., vol. 115, pp. 6317–6321, 1993.

Kiefer et al, *Negative Screening for Sickle Cell Diseases with a Monoclonal Immunoassay on Newborn Blood Eluted from Filter Paper*, J. Lab. Clin. Med., vol. 116, No. 6, pp. 826–830, Dec. 1990.

Kim et al, *Influence of Charge on the Rate of Amide Proton Exchange*, Biochemistry, vol. 21, No. 1, pp. 1–5, Jan. 5, 1982.

Kirley, *Reduction and Fluorescent Labeling of Cyst(e)ine–Containing Proteins for Subsequent Structural Analyses*, Analytical Biochemistry, vol. 180, pp. 231–236, 1989.

Krishnan et al, *Purification of an Acid Protease and a Serine Carboxypeptidase from Aspergillus Niger Using Metal–Chelate Affinity Chromatography*, Journal of Chromatography, vol. 329, pp. 165–170, 1985.

Levison et al, *Reduction of Biological Substances by Water–Soluble Phosphines: Gamma Globulin (IgG)*, Experientia, vol. 25, pp. 126–127, 1969.

Loo et al, *Primary Sequence Information from Intact Proteins by Electrospray Ionization Tandem Mass Spectrometry*, Science, vol. 248, pp. 201–204, Apr. 13, 1990.

Louie et al, *Allosteric Energy at the Hemoglobin Beta Chain C Terminus Studied by Hydrogen Exchange*, J. Mol. Biol., vol. 201, pp. 755–764, 1988.

Louie et al, *Salt, Phosphate and the Bohr Effect at the Hemoglobin Beta Chain C Terminus Studied by Hydrogen Exchange*, J. Mol. Biol., vol. 201, pp. 765–772, 1988.

Mallikarachchi et al, *Effects of ATP and CTP on the Conformation of the Regulatory Subunit of Escherichia coli Aspartate Transcarbamylase in Solution: A Medium–Resolution Hydrogen Exchange Study*, Biochemistry, vol. 28, pp. 5386–5391, 1989.

Mayne et al, *Effect of Antibody Binding on Protein Motions Studied by Hydrogen–Exchange Labeling and Two–Dimensional NMR*, Biochemistry, vol. 31, pp. 10678–10685, 1992.

McCloskey, *Introduction of Deuterium by Exchange for Measurement by Mass Spectrometry*, Methods in Enzymology, vol. 193, pp. 329–338, 1990.

McCormick et al, *Hemoglobin Binding with Haptoglobin: Delineation of the Haptoglobin Binding Site on the α chain of Human Hemoglobin*, Journal of Protein Chemistry, vol. 9, No. 6, pp. 735–742, 1990.

Molday et al, *Primary Structure Effects on Peptide Group Hydrogen Exchange*, Biochemistry, vol. 11, No. 2, pp. 150–158, 1972.

Patterson et al, *An Antibody Binding Site on Cytochrome c Defined by Hydrogen Exchange and Two–Dimensional NMR*, Science, vol. 249, pp. 755–759, Aug. 17, 1990.

Ray et al, *Allosteric Sensitivity in Hemoglobin at the α–Subunit N–Terminus Studied by Hydrogen Exchange*, Biochemistry, vol. 25, pp. 3000–3007, 1986.

Rogero et al, *Individual Breathing Reactions Measured by Functional Labeling and Hydrogen Exchange Methods*, Methods in Enzymology, vol. 131, pp. 508–517, 1986.

Rosa et al, *An Experimental Procedure for Increasing the Structural Resolution of Chemistry Hydrogen–exchange Measurements on Proteins: Application to Ribonuclease S Peptide*, J. Mol. Biol., vol. 133, pp. 399–416, 1979.

Rosa et al, *Effects of Binding of S–Peptide and 2'–Cytidine Monophosphate on Hydrogen Exchange from the S–Protein Component of Ribonuclease S*, J. Mol. Biol., vol. 160, pp. 517–530, 1982.

Rosa et al, *Hydrogen Exchange from Identified Regions of the S–Protein Component of Ribonuclease as a Function of Temperature, pH, and Binding of S–Peptide*, J. Mol. Biol., vol. 145, pp. 835–851, 1981.

Rosnack et al, *C–Terminal Sequencing of Peptides Using Electrospray Ionization Mass Spectrometry*, Rapid Communications in Mass Spectrometry, vol. 6, pp. 637–640, 1992.

Ruegg et al, *Reductive Cleavage of Cystine Disulfides with Tributylphosphine*, Meth. Enzymol., vol. 47, pp. 111–117, 1977.

Schreier et al, *Concentration–Dependent Hydrogen Exchange Kinetics of H–labeled S–Peptide in Ribonuclease S*, J. Mol. Biol., vol. 105, pp. 409–426, 1976.

Sepetov et al, *The Use of Hydrogen–Deuterium Exchange to Facilitate Peptide Sequencing by Electrospray Tandem Mass Spectrometry*, Rapid Communications in Mass Spectrometry, vol. 7, pp. 58–62, 1993.

Smith et al, *Carboxy–Terminal Protein Sequence Analysis using Carboxypeptidase P and Electrospray Mass Spectrometry*, Techniques in Protein Chemistry IV, pp. 463–470, 1993.

Takahashi et al, *Cathepsin D from Porcine and Bovine Spleen*, Methods In Enzymology, vol. 80, pp. 565–581, 1981.

Thevenon–Emeric et al, *Determination of Amide Hydrogen Exchange Rates in Peptides by Mass Spectrometry*, Anal. Chem., vol. 64, pp. 2456–2458, 1992.

Tsugita, *Developments in Protein Microsequencing*, Adv. Biophys., vol. 23, pp. 81–113, 1987.

Tsugita et al, *Develpment of Novel C–Terminal Sequencing Methods*, Methods in Protein Sequence Analysis, edited by K Imahori, F Sakiyama, Plenum Press, New York, pp. 55–62 1993.

Tsugita et al, *Reaction of Pentafluoropropionic Anhydride Vapor on Polypeptide as Revealed by Mass Spectrometry. A Carboxypeptidase Mimetic Degradation*, Chemistry Letters, pp. 235–238, 1992.

Winger et al, *Probing Qualitative Conformation Differences of Multiply Protonated Gas–Phase Proteins via H/D Isotopic Exchange with $D_2O$*, J. Am. Chem. Soc., vol. 114, pp. 5897–5898, 1992.

Xiaoming et al, *A Novel Carboxylesterase From Aspergillus Niger and its Hydrolysis of Succinimide Esters*, Carlsberg Res. Commun., vol. 54, pp. 241–249, 1989.

Yoshioka et al, *Haemoglobin Binding with Haptoglobin*, Biochemistry J., vol. 234, pp. 453–456, 1986.

Zhang et al, *Determination of Amide Hydrogen Exchange by Mass Spectrometry: A New Tool for Protein Structure Elucidation*, Protein Science, vol. 2, pp. 522–531, 1993.

Zhu et al, *Purification and Characterization of an Extracellular Acid Proteinase from the Ectomycorrhizal Fungus Hebeloma Crustuliniforme*, Applied and Environmental Microbiology, vol. 56, pp. 837–843, Apr. 1990.

Carrey, p. 132, in *Protein Structure, A Practical Approach*, Ed. Creighton, IRL p. 110 at Oxford University Press (1989).

HLPC OD
TRACING

HEMOGLOBIN ALONE
4 hr on, 0 hr off

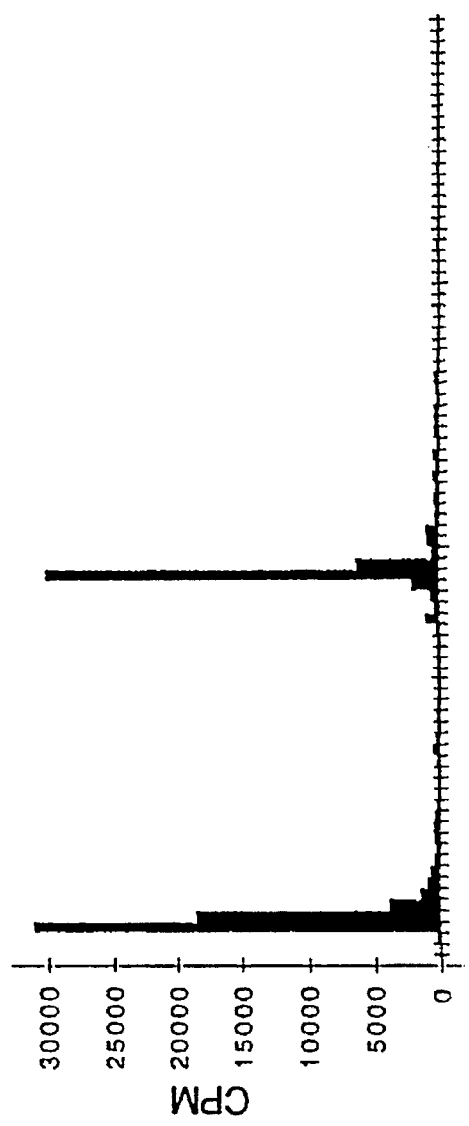
Fig. 1c. HEMOGLOBIN 4 hr on, add monoclonal β6, 40 hr off
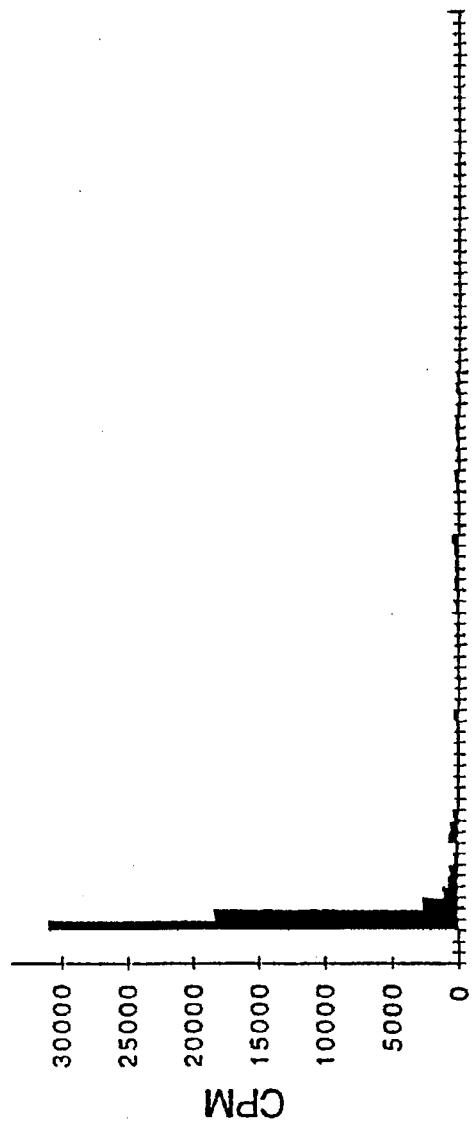
Fig. 1d. HEMOGLOBIN ALONE 4 hr on, 40 hr off

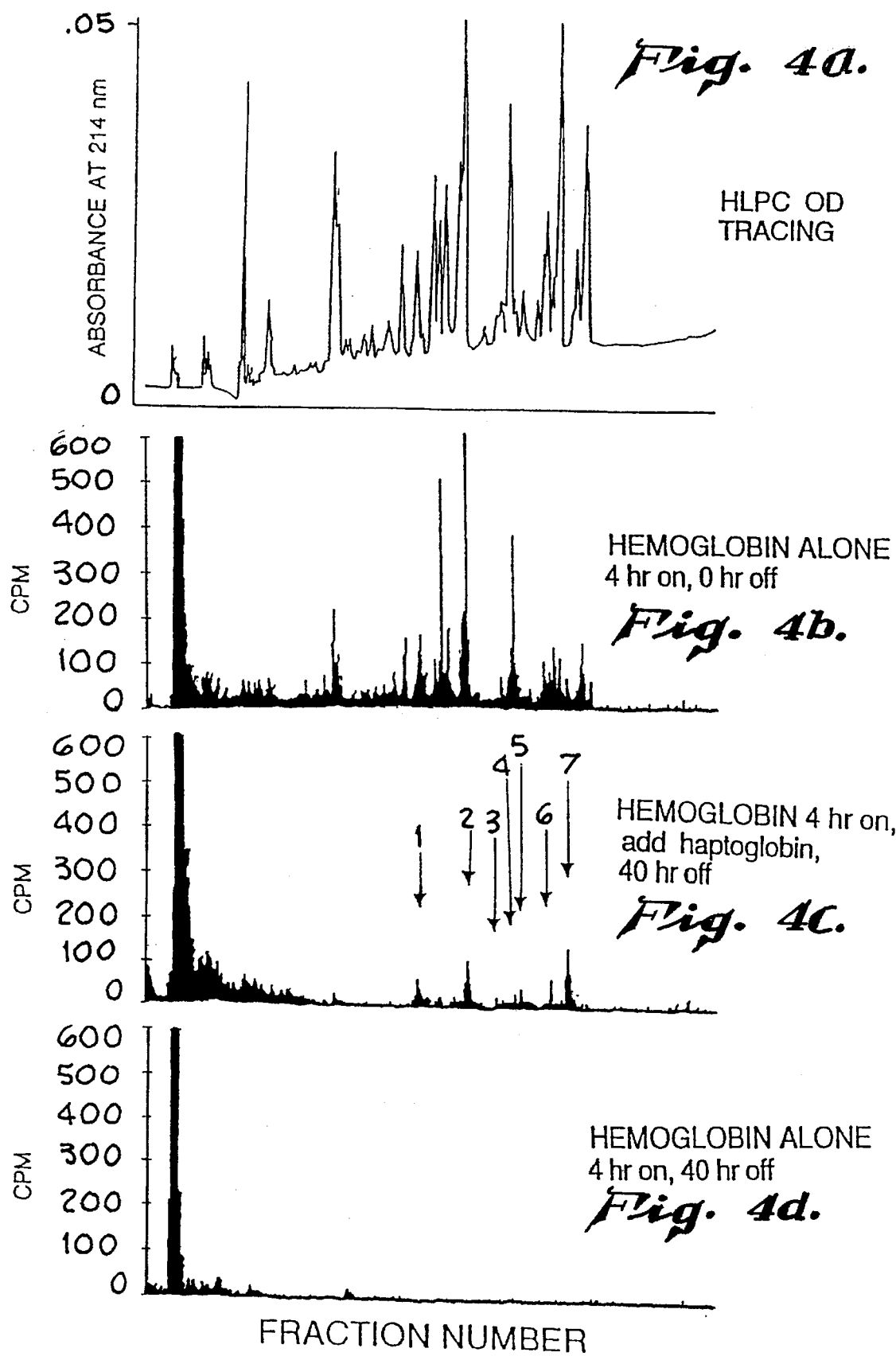

Hb plus β6 Monoclonal

Hb plus β121 Monoclonal

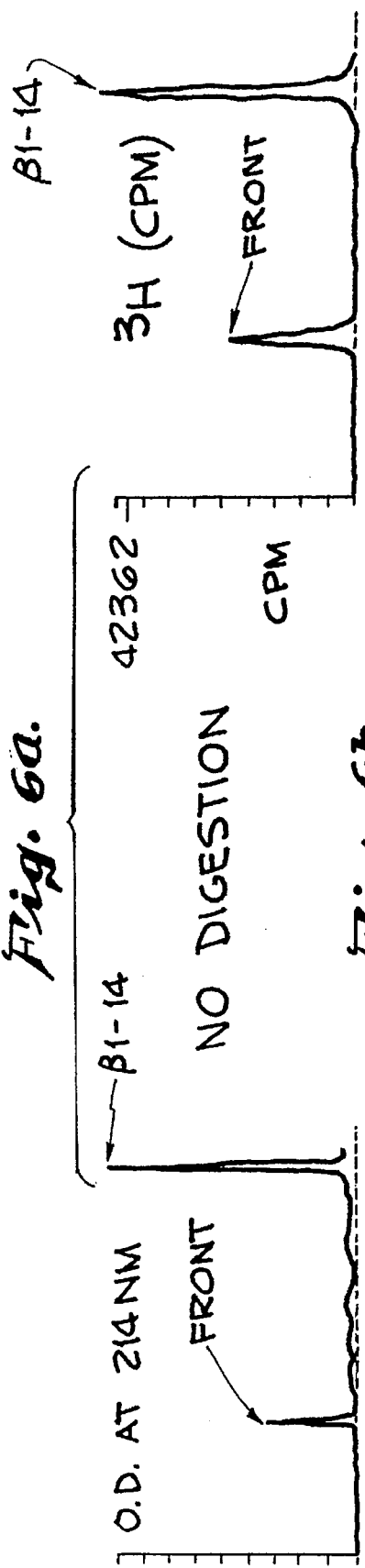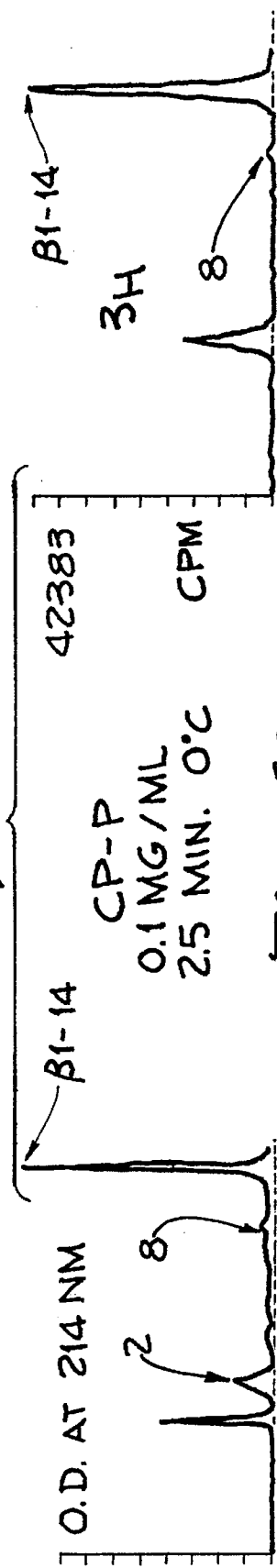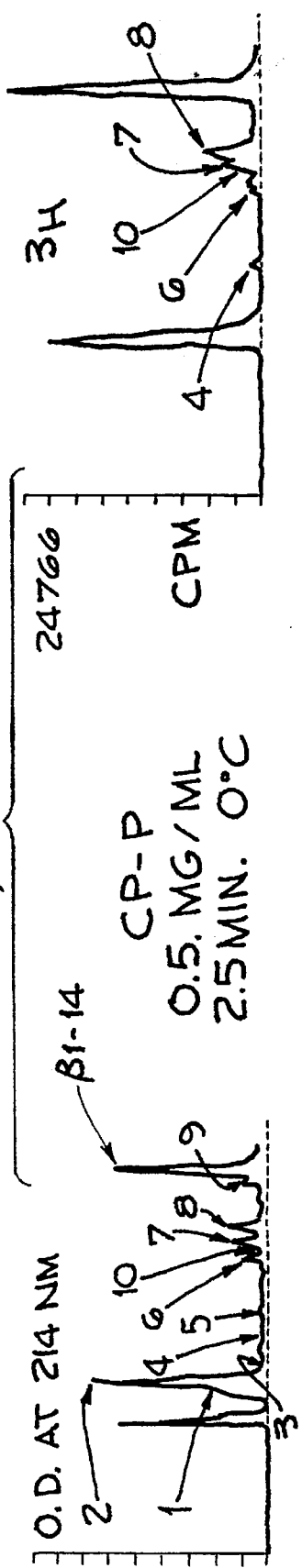
Fig. 6a. NO DIGESTION
Fig. 6b. CP-P 0.1 MG/ML 2.5 MIN. 0°C
Fig. 6c. CP-P 0.5 MG/ML 2.5 MIN. 0°C

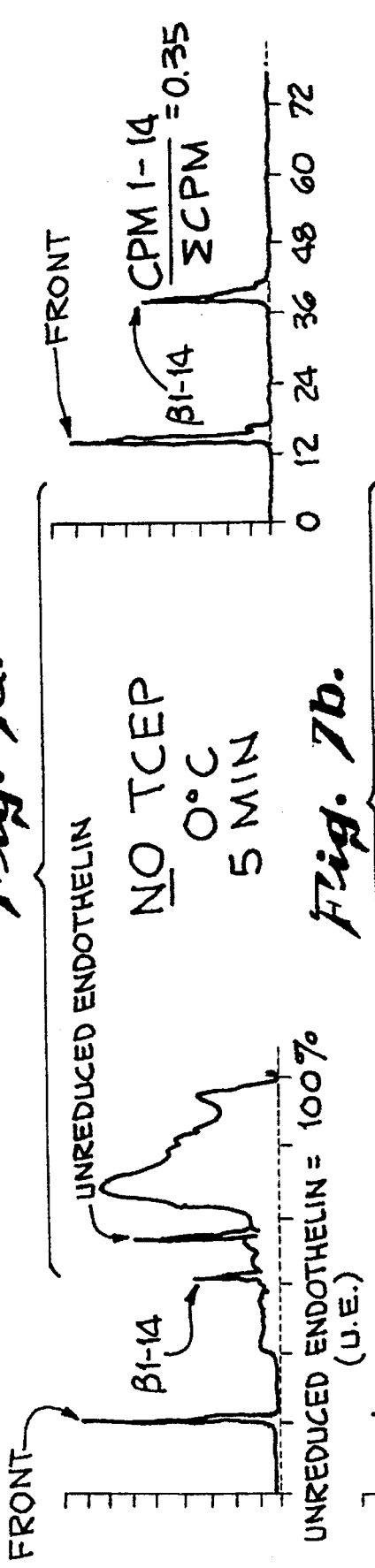
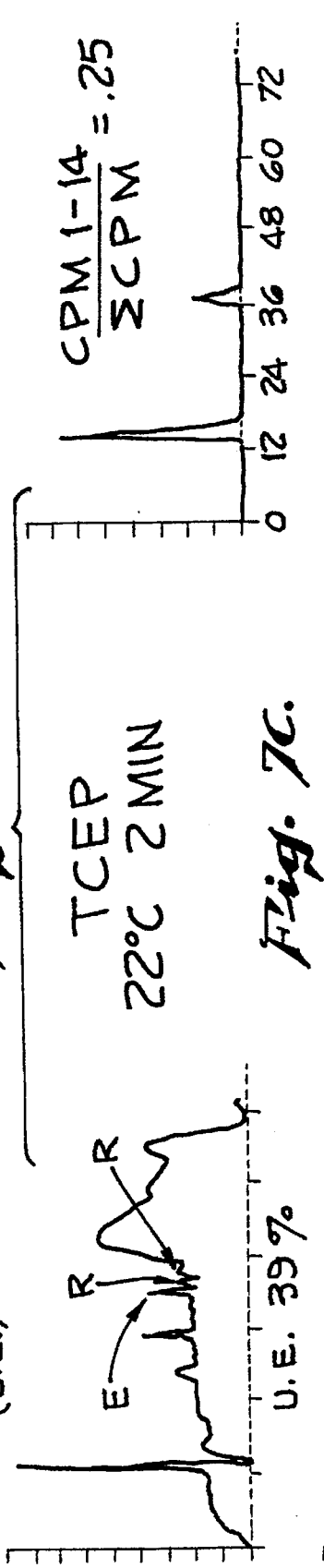
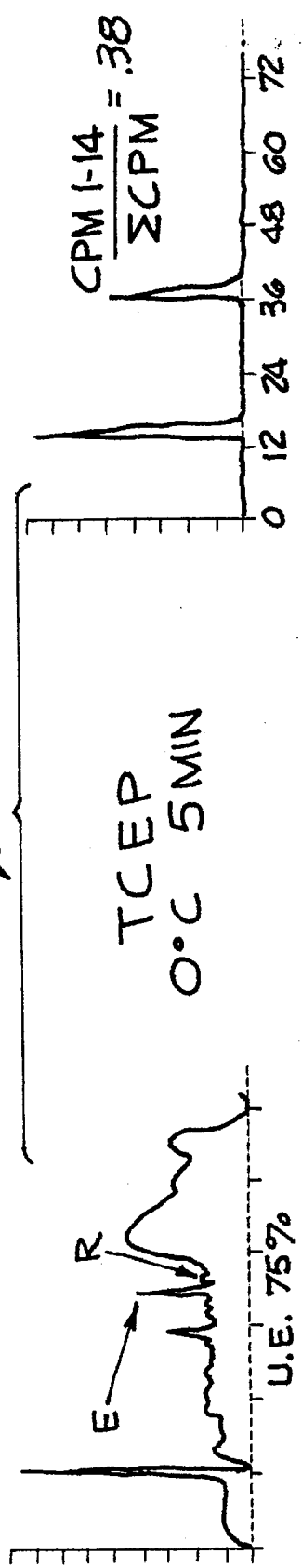
Fig. 7a. NO TCEP 0°C 5 MIN
Fig. 7b. TCEP 22°C 2 MIN
Fig. 7c. TCEP 0°C 5 MIN

METHOD FOR CHARACTERIZATION OF THE FINE STRUCTURE OF PROTEIN BINDING SITES

This invention was made with Government support under Grant No. HL-30480, awarded by the National Institutes of Health. The Government has certain rights in this invention.

BACKGROUND OF THE INVENTION

1. Field of the Invention

The present invention relates to the characterization of the binding site involved in binding between a binding protein and a binding partner.

2. Background Art

Biochemical Binding, Generally

Many biological processes are mediated by noncovalent binding interactions between a protein and another molecule, its binding partner. The identification of the structural features of the two binding molecules which immediately contribute to those interactions would be useful in designing drugs which alter these processes.

The molecules which preferentially bind each other may be referred to as members of a "specific binding pair". Such pairs include an antibody and its antigen, a lectin and a carbohydrate which it binds, an enzyme and its substrate, and a hormone and its cellular receptor. In some texts, the terms "receptor" and "ligand" are used to identify a pair of binding molecules. Usually, the term "receptor" is assigned to a member of a specific binding pair which is of a class of molecules known for its binding activity, e.g., antibodies. The term "receptor" is also preferentially conferred on the member of the pair which is larger in size, e.g., on avidin in the case of the avidin-biotin pair. However, the identification of receptor and ligand is ultimately arbitrary, and the term "ligand" may be used to refer to a molecule which others would call a "receptor". The term "anti-ligand" is sometimes used in place of "receptor".

While binding interactions may occur between any pair of molecules, e.g., two strands of DNA, the present specification is primarily concerned with interactions in which at least one of the molecules is a protein. Hence, it is convenient to speak of a "binding protein" and its "binding partner". The term "protein" is used herein in a broad sense which includes, mutatis mutandis, polypeptides and oligopeptides, and derivatives thereof, such as glycoproteins, lipoproteins, and phosphoproteins. The essential requirement is that the "binding protein" feature one or more peptide (—NHCO—) bonds, as the amide hydrogen of the peptide bond (as well as in the side chains of certain amino acids) has certain properties which lends itself to analysis by proton exchange.

A "binding site" is a point of contact between a binding surface ("paratope") of the binding protein and a complementary surface ("epitope") of the binding partner. (When the binding partner is a protein, the designation of "paratope" and "epitope" is essentially arbitrary. However, in the case of antibody-antigen interactions, it is conventional to refer to the antigen binding site of the antibody as the "paratope" and the target site on the antigen as the "epitope".) A specific binding pair may have more than one binding site, and the term "pair" is used loosely, as the binding protein may bind two or more binding partners (as in the case of a divalent antibody). Moreover, other molecules, e.g., allosteric effectors, may alter the conformation of a member of the "pair" and thereby modulate the binding. The term "pair" is intended to encompass these more complex interactions.

Limitations of Current Methods of Characterizing Protein Binding Sites

Considerable experimental work and time are required to precisely characterize a binding site. In general, the techniques which are the easiest to use and which give the quickest answers, result in an inexact and only approximate idea of the nature of the critical structural features. Techniques in this category include the study of proteolytically generated fragments of the protein which retain binding function; recombinant DNA techniques, in which proteins are constructed with altered amino acid sequence (site directed mutagenesis); epitope scanning peptide studies (construction of a large number of small peptides representing subregions of the intact protein followed by study of the ability of the peptides to inhibit binding of the ligand to receptor); covalent crosslinking of the protein to its binding partner in the area of the binding site, followed by fragmentation of the protein and identification of crosslinked fragments; and affinity labeling of regions of the receptor which are located near the ligand binding site of the receptor, followed by characterization of such "nearest neighbor" peptides. (Reviewed in 1, 2).

These techniques work best for the determination of the structure of binding subregions which are simple in nature, as when a single short contiguous stretch of polypeptide within a protein is responsible for most of the binding activity. However, for many protein-binding partner systems of current interest, the structures responsible for binding on both receptor and ligand or antibody are created by the complex interaction of multiple non-contiguous peptide sequences. The complexities of these interactions may confound conventional analytical techniques, as binding function is often lost as soon as one of the 3-dimensional conformations of the several contributing polypeptide sequences is directly or indirectly perturbed.

The most definitive techniques for the characterization of the structure of receptor binding sites have been NMR spectroscopy and X-ray crystallography. While these techniques can ideally provide a precise characterization of the relevant structural features, they have major limitations, including inordinate amounts of time required for study, inability to study large proteins, and, for X-ray analysis, the need for protein-binding partner crystals (Ref. 3).

Applicant's technology overcomes these limitations and allows the rapid identification of each of the specific polypeptides and amino acids within a protein which constitute its protein ligand binding site or antibody binding subregion in virtually any protein-ligand system or protein antigen-antibody system, regardless of the complexity of the binding sites present or the size of the proteins involved. This technology is superior in speed and resolution to currently employed biochemical techniques.

Tritium Exchange

When a protein in its native folded state is incubated in buffers containing tritiated water, tritium in the buffer reversibly exchanges with hydrogen present in the protein at acidic positions (for example, O—H, S—H, and N—H groups) with rates of exchange which are dependent on each exchangeable proton's chemical environment, temperature, and most importantly, its accessibility to the tritiated water in the buffer. (Refs. 4, 5) Accessibility is determined in turn by both the surface (solvent-exposed) disposition of the proton, and the degree to which it is hydrogen-bonded to other regions of the folded protein. Simply stated, acidic protons present on amino acid residues which are on the outside (buffer-exposed) surface of the protein and which are hydrogen-bonded to solvent water will exchange more rapidly with tritium in the buffer than will similar acidic protons which are buried and hydrogen-bonded within the folded protein.

Proton exchange reactions can be greatly accelerated by both acid and base-mediated catalysis, and the rate of exchange observed at any particular pH is the sum of both acid and base mediated mechanisms. For many acidic protons, a pH in the range of 2.7 results in an overall minimum rate of exchange (Ref. 6, pg.238, FIG. 3, refs. 7–11). While hydrogens in protein hydroxyl and amino groups exchange with tritium in buffer at millisecond rates, the exchange rate of one particular acidic proton, the peptide amide bond proton, is considerably slower, having a half life of exchange (when freely hydrogen bonded to solvent water) of approximately 0.5 seconds at 0° C., pH 7, which is greatly slowed to a half life of exchange of 70 minutes at 0° C. pH 2.7.

When peptide amide protons are buried within a folded protein, or are hydrogen bonded to other parts of the protein, exchange half lives with solvent protons are often considerably lengthened, at times being measured in hours to days. Proton exchange at peptide amides is a fully reversible reaction, and rates of on-exchange (solvent tritium replacing protein-bound hydrogen) are identical to rates of off-exchange (hydrogen replacing protein-bound tritium) if the state of a particular peptide amide within a protein, including its chemical environment and accessibility to solvent protons, remains identical during on-exchange and off-exchange conditions.

Tritium exchange techniques have been extensively used for the measurement of peptide amide exchange rates within an individual protein (reviewed in 4). The rates of exchange of other acidic protons (OH, NH, SH) are so rapid that they cannot be followed in these techniques and all subsequent discussion refers exclusively to peptide amide proton exchange. In these studies, purified proteins are on-exchanged by incubation in buffers containing tritiated water for varying periods of time, transferred to buffers free of tritium, and the rate of off-exchange of tritium determined. By analysis of the rates of tritium on- and off-exchange, estimates of the numbers of peptide amide protons in the protein whose exchange rates fall within particular exchange rate ranges can be made. These studies do not allow a determination of the identity (location within the protein's primary amino acid sequence) of the exchanging amide hydrogens measured.

Extensions of these techniques have been used to detect the presence within proteins of peptide amides which experience allosterically-induced changes in their local chemical environment and to study pathways of protein folding (5, 12–14). For these studies, tritium on-exchanged proteins are allowed to off-exchange after they have experienced either an allosteric change in shape, or have undergone time-dependent folding upon themselves, and the number of peptide amides which experience a change in their exchange rate subsequent to the allosteric/folding modifications determined. Changes in exchange rate indicate that alterations of the chemical environment of particular peptide amides have occurred which are relevant to proton exchange (solvent accessibility, hydrogen bonding etc.). Peptide amides which undergo an induced slowing in their exchange rate are referred to as "slowed amides" and if previously on-exchanged tritium is sufficiently slowed in its off-exchange from such amides there results a "functional tritium labeling" of these amides. From these measurements, inferences are made as to the structural nature of the shape changes which occurred within the isolated protein. Again, determination of the identity of the particular peptide amides experiencing changes in their environment is not possible with these techniques.

Four groups of investigators have described technical extensions (collectively referred to as medium resolution tritium exchange) which allow the locations of particular slowed, tritium labeled peptide amides within the primary sequence of small proteins to be localized to a particular proteolytic fragment, though not to a particular amino acid.

Rosa and Richards were the first to describe and utilize medium resolution tritium techniques in their studies of the folding of ribonuclease S protein fragments (15–17). However, the techniques described by Rosa and Richards were of marginal utility, primarily due to their failure to optimize certain critical experimental steps (reviewed in 6, pg 238, 244). No studies employing related techniques were published until the work of Englander and co-workers in which extensive modifications and optimizations of the Rosa and Richards technique were first described.

Englander's investigations utilizing tritium exchange have focused exclusively on the study of allosteric changes which take place in tetrameric hemoglobin ($\alpha$ subunit and $\beta$ subunit 16 kD in size each) upon deoxygenation (6,18–21). In the Englander procedure, native hemoglobin (milligram quantities) in the oxygenated state is on-exchanged in tritiated water of relatively low specific activity (2–100 mCi/ml). The hemoglobin is then deoxygenated (inducing allosteric change), transferred to tritium-free buffers by gel permeation column chromatography, and then allowed to out-exchange for 10–50 times the on-exchange time. On-exchanged tritium present on peptide amides which experience no change in exchange rate subsequent to the induced allosteric change in hemoglobin structure off-exchanges at rates identical to its on-exchange rates, and therefore is almost totally removed from the protein after the long off-exchange period. However, peptide amides which experience slowing of their exchange rate subsequent to the induced allosteric changes preferentially retain the tritium label during the period of off-exchange.

To localize (in terms of hemoglobin's primary sequence) the slowed amides bearing the residual tritium label, Englander then proteolytically fragments the off-exchanged hemoglobin with the protease pepsin, separates, isolates and identifies the various peptide fragments by reverse phase high pressure liquid chromatography (RP-HPLC), and determines which fragments bear the residual tritium label by scintillation counting. However, as the fragmentation of hemoglobin proceeds, each fragment's secondary and tertiary structure is lost and the unfolded peptide amides become freely accessible to $H_2O$ in the buffer. At physiologic pH (>6), any amide-bound tritium label would leave the unfolded fragments within seconds. Englander therefore performs the fragmentation and HPLC peptide isolation procedures under conditions which he believes minimize peptide amide proton exchange, including cold temperature (4° C.) and use of phosphate buffers at pH 2.7 (reviewed in 6). This technique has been used successfully by Englander to coarsely identify and localize the peptidic regions of hemoglobin $\alpha$ and $\beta$ chains which participate in deoxygenation-induced allosteric changes (18–21). The ability of the Englander technique to localize tritium labeled amides, while an important advance, remains low; at the best, Englander reports that his technique localizes amide tritium label to hemoglobin peptides 14 amino acids or greater in size, without the ability to further sublocalize the label.

In Englander's work, there is no appreciation that a suitably adapted tritium exchange technique might be used to identify the peptide amides which reside in the contacting surface of a protein receptor and its binding partner: his disclosures are concerned exclusively with the mapping of allosteric changes in hemoglobin. Furthermore, based on his optimization studies (6–11, 13), Englander teaches and warns that a pH of 2.7 must be employed in both the proteolysis and HPLC steps, necessitating the use of proteases which are functional at these pH's (acid proteases). Unfortunately, acid proteases are relatively nonspecific in their sites of proteolytic cleavage, leading to the production of a very large number of different peptide fragments and hence to considerable HPLC separation difficulties. The constraint of performing the HPLC separation step at pH 2.7 greatly limits the ability to optimize the chromatographic separation of multiple overlapping peptides by varying the pH at which HPLC is performed. Englander tried to work around these problems, for the localization of hemoglobin peptides experiencing allosteric changes, by taking advantage of the fact that some peptide bonds are somewhat more sensitive to pepsin than others. He therefore limits the duration of exposure of the protein to pepsin to reduce the number of fragments. Even then the fragments were "difficult to separate cleanly". They were also, of course, longer (on average), and therefore the resolution was lower. He also tried to simplify the patterns by first separating the alpha and beta chains of hemoglobin. However, there was a tradeoff: increased tritium loss during the alpha-beta separation and the removal of the solvent, preparatory to proteolysis. Englander concludes, "At present the total analysis of the HX (hydrogen exchange) behavior of a given protein by these methods is an immense task. In a large sense, the best strategies for undertaking such a task remain to be formulated. Also, these efforts would benefit from further technical improvements, for example in HPLC separation capability and perhaps especially in the development of additional acid proteases with properties adapted to the needs of these experiments" (6).

Over the succeeding seven years since this observation was made, no advances have been disclosed which address these critical limitations of the medium resolution tritium exchange technique. It has been perceived that improvements to the HPLC separation step were problematic due to the constraint of working at pH 2.7. The current limited success with small proteins has made it pointless to attempt similar studies of larger proteins where the problems of inadequate HPLC peptide separation at pH 2.7, and imprecision in the ability to sublocalize labeled amides would be greatly compounded. Furthermore, most acid-reactive proteases are in general no more specific in their cleavage patterns than pepsin and efforts to improve the technology by employing other acid reactive proteases other than pepsin have not significantly improved the technique. Given these limitations of medium resolution tritium exchange art, no studies have been disclosed which utilize proteins with subunit size greater than 16 kilodaltons.

Allewell and co-workers have disclosed studies utilizing the Englander techniques to localize induced allosteric changes in the enzyme *escherichia coli* aspartate transcarbamylase (22,23). Burz, et al. (22) is a brief disclosure in which the isolated R2 subunit of this enzyme is on-exchanged in tritiated buffer of specific activity 100 mCi/ml, allosteric change induced by the addition of ATP, and then the conformationally altered subunit off-exchanged. The enzyme R2 subunit was then proteolytically cleaved with pepsin and analyzed for the amount of label present in certain fragments. Analysis employed techniques which rigidly adhered to the recommendations of Englander, utilizing a single RP HPLC separation in a pH 2.8 buffer.

The authors note difficulty in separating the large number of peptides generated, even from this small protein subfragment, given the constraints of the Englander methodology. They comment that "the principal limitation of this method at present is the separation with columns now available". ATP binding to the enzyme was shown to alter the rate of exchange of hydrogens within several relatively large peptidic fragments of the R2 subunit. In a subsequent more complete disclosure (23), the Allewell group discloses studies of the allosteric changes induced in the R2 subunit by both ATP and CTP. They disclose on-exchange of the R2 subunit in tritiated water-containing buffer of specific activity 22–45 mCi/ml, addition of ATP or CTP followed by off exchange of the tritium in normal water-containing buffer. The analysis comprised digestion of the complex with pepsin, and separation of the peptide fragments by reverse phase HPLC in a pH 2.8 or pH 2.7 buffer, all of which rigidly adheres to the teachings of Englander. Peptides were identified by amino acid composition or by N-terminal analysis, and the radioactivity of each fragment was determined by scintillation counting. In both of these studies the localization of tritium label was limited to peptides which averaged 10–15 amino acids in size, without higher resolution being attempted.

Finally, Beasty, et al. (24) have disclosed studies employing tritium exchange techniques to study folding of the α subunit of *E. Coli* tyrptophan synthetase. The authors employed tritiated water of specific activity 20 mCi/ml, and fragmented the tritium labeled enzyme protein with trypsin at a pH 5.5, conditions under which the protein and the large fragments generated retained sufficient folded structure as to protect amide hydrogens from off exchange during proteolysis and HPLC analysis. Under these conditions, the authors were able to produce only 3 protein fragments, the smallest being 70 amino acids in size. The authors made no further attempt to sublocalize the label by further digestion and/or HPLC analysis. Indeed, under the experimental conditions they employed (they performed all steps at 12° C. instead of 4° C., and performed proteolysis at pH 5.5 instead of pH in the range of 2–3), it would have been impossible to further sublocalize the labeled amides by tritium exchange, as label would have been immediately lost (off-exchanged) by the unfolding of subsequently generated proteolytic fragments at pH 5.5 if they were less than 10–30 amino acids in size.

In summary, the above disclosures are restricted to studies of medium resolution tritium exchange of: 1) The re-folding on itself of different parts of an individual protein (tryptophan synthetase α subunit) (24); 2) The re-folding onto itself of two fragments proteolytically generated from the same protein (ribonuclease-S) (15–17); 3) The changes in shape (allosteric change) which an individual protein (hemoglobin) underwent subsequent to removal of oxygen (hemoglobin) (4–6,12–14,18–21); and 4) The allosteric changes in a protein after the addition of known allosteric change inducers (aspartate transcarbamylase) (22,23).

Because tritium exchange art was limited in its ability to study large proteins, none of these or other investigators disclosed or proposed that tritium exchange techniques could be adapted to effectively study contact surfaces between two different, large proteins (subunits >16 kD in size) or that peptide amides functionally labeled with tritium in large protein-binding partner interactions could effectively be localized precisely at the amino acid sequence level.

Fromageot, et al., U.S. Pat. No. 3,828,102 (25) discloses using hydrogen exchange to tritium label a protein and its binding partner. The protein-binding partner complex is formed before allowing on-exchange to occur and thus the binding site is not selectively labeled. In the present invention the protein is on-exchanged before its interaction with binding partner and subsequent off-exchange, and thus, the peptide amides which reside in the interactions surface specifically retain label while other sites do not.

Benson, U.S. Pat. Nos. 3,560,158 and 3,623,840 (26) disclose using hydrogen exchange to tritiate compounds for analytical purposes. These references differ from the invention by not providing any mechanism for distinguishing between any potential binding site and the rest of the molecule.

NMR-Deuterium Techniques to Study Protein-Binding Partner Interactions

Fesik, et al (27) discloses measuring by NMR the hydrogen (deuterium) exchange of a peptide before and after it is bound to a protein. From this data, the interactions of various hydrogens in the peptide with the binding site of the protein are analyzed.

Patterson, et al. (28) and Mayne, et al. (29) disclose NMR mapping of an antibody binding site on a protein (cytochrome-C) using deuterium exchange. This relatively small protein, with a solved NMR structure, is first complexed to anti-cytochrome-C monoclonal antibody, and the preformed complex then incubated in deuterated water-containing buffers and NMR spectra obtained at several time intervals. The NMR spectra of the antigen-antibody complex is examined for the presence of peptide amides which experience slowed hydrogen exchange with solvent deuterium as compared to their rate of exchange in uncomplexed native cytochrome-C. Benjamin, et al. (30) employ an identical NMR-deuterium technique to study the interaction of hen egg lysosozyme (HEL) with HEL-specific monoclonal antibodies. While both this NMR-deuterium technique, and medium resolution tritium exchange rely on the phenomenon of proton exchange at peptide amides, they utilize radically different methodologies to measure and localize the exchanging amides. Furthermore, study of proteins by the NMR technique is not possible unless the protein is small (less than 30 kD), large amounts of the protein are available for the study, and computationally intensive resonance assignment work is completed.

Recently, others (45–50) have disclosed techniques in which exchange-deuterated proteins are incubated with binding partner, off-exchanged, the complex fragmented with pepsin, and deuterium-bearing peptides identified by single stage Fab or electrospray MS. In these studies, no attempt has been made to sublocalize peptide-bound deuterium within pepsin-generated peptides.

SUMMARY OF THE INVENTION

The present invention provides for substantially higher resolution of the sites of functional tritium labeling, and provides a method for the functional labeling of specific amino acid residues that participate in binding protein-binding partner interactions. It is particularly suitable for the study of the binding protein-binding partner subregions of large (>30 KD) proteins, even in small quantities. This result is achieved by the use, singly or in combination, of the improvements described below.

Applicant has discovered that the art has overstated the sensitivity of the tritium label to pH. Englander (10) reported that at 0° C., the tritium label was most stable (when the tritiated protein was placed in an untritiated aqueous buffer) at pH 2.7, and that the rate of off-exchanged increased rapidly (10 fold per pH unit) as one moved away from that pH. Surprisingly, Applicant found that at 0° C., the label was sufficiently stable to permit analysis even at a pH of 2.1. While the acceptable pH range will vary with temperature, and the choice of solvent (the optimal pH increases if a polar nonaqueous solvent is introduced), the fact remains that pH was previously considered to be essentially fixed. Since the tritium label is stable over a broader pH range, it is possible to depart from Englander's recommended pH seeking HPLC conditions which result in effective separation of the peptide fragments. Moreover, Applicants have found that resolution is greatly improved by resorting to a two-dimensional HPLC separation, at two substantially different pHs, e.g., 2.7 and 2.1.

When the binding molecules are large, so many different fragments are obtained after proleolytic digest that the individual peaks on a single HPLC separation are heterogeneous. A two-dimensional HPLC separation, at two different pH values, greatly improves resolution of the individual fragments. It allows high efficiency purification of tritium label bearing-peptides from the enormous number of unlabeled peptides generated by peptic fragmentation of large proteins. Two-dimensional separation of molecules is known in the chromatographic art. However, despite frequent complaints in the Tritium exchange literature about resolution problems, 2D separations have not been employed previously in connection with Tritium exchange.

A second improvement is the finer localization of the tritium labels achieved by analysis of subfragments generated by controlled, stepwise, carboxypeptidase digestion of each isolated, tritium-labeled peptide fragment. This procedure was not used in any of the cited references to further localize the labeling sites, though improved resolution was certainly a goal of the art. The closest the art comes is Englander's general suggestions of further fragmentations with another "acid protease".

While carboxypeptidases have been used in peptide sequencing, the need to minimize tritium losses forbids use of carboxypeptidases which are inactivated by acidic (pH 2.7) buffers. However, carboxypeptidase-P is suitable for proteolysis of peptides under acidic conditions. Exhaustive subfragmentation of purified tritium label-bearing peptides is performed with acid-resistant carboxypeptidases under conditions that produce a complete set of amide-labeled daughter peptides each shorter than the preceding one by a single carboxy-terminal amino acid. HPLC analysis of the several members of this set of progressively truncated peptides allows the reliable assignment of label to particular amide positions within the parent peptide. Alternatively, the present invention contemplates C-terminal chemical degradation techniques that can be performed at 0° C. and "slow proton exchange compatible" acidic pH, e.g., by pentafluoropropionic acid anhydride.

Another important feature is that the on-exchange occurs before formation of the complex, and the off-exchange occurs afterward. As a result, only the binding site remains tritiated. Since the binding site is normally only a small portion of the molecules. A higher signal-to-background ratio is obtained with this approach than with Englander's more conventional procedure.

The applicant has discovered that water soluble phosphines may be used to disrupt a protein's disulfide bonds under "slow proton exchange" conditions. This allows much more effective peptic fragmentation of large proteins which contain disulfide bonds without causing tritium label to be lost from the protein or its proteolytic fragments (as would be the case with conventional disulfide reduction techniques which must be performed at pH's which are very unfavorable for preservation of tritium label).

The sensitivity of the technique may be improved by the use of synthetic peptides as HPLC mobility markers. A set of carboxy-terminal truncated peptides, consisting of all possible daughter peptides which can be generated by carboxy-terminal digestion of a parent peptide, is synthesized and used to infer the identity of HPLC separated, carboxypeptidase-generated functionally labeled daughter peptides. This allows unambiguous identification of carboxypeptide-generated peptide fragments which are detectable spectrophotometrically, but proteolytically produced in quantities insufficient for direct identification by amino acid analysis.

Other improvements worthy of mention, although not required for success, include the use of tritiated water of high specific activity, thereby increasing sensitivity, and trimming the binding protein-binding partner, complex by proteolytic agents (chemical or enzymatic), prior to "off-exchange", to remove irrelevant segments.

The identity of each of the several carboxy-terminus-truncated peptides is determined by amino acid analysis, peptide sequencing, or through the use of synthetic HPLC mobility marker peptides, and the amount of tritium label attached to each c-terminal truncated peptide determined by scintillation counting. In this manner, the precise location, within the protein, of each peptide amide that is functionally labeled with tritium by virtue of its interaction with binding partner is determined.

In an additional embodiment, functionally labeled proteolytic fragments, generated from a protein that has been functionally labeled with deuterium and/or tritium by receptor-ligand complex formation, are analyzed by fast atom bombardment (FAB) or electrospray mass spectroscopy. The applicants have recognized that it is possible to conduct Fast Atom Bombardment (FAB) or electrospray mass spectroscopy under conditions which minimize off-exchange of peptide amide deuterium from peptide fragments and allow the direct determination of the location of functionally attached label within a peptide in the size range 3–30 amino acids. Furthermore, mass spectroscopy can itself resolve peptide fragments which co-migrate on HPLC, and allow for precise delineation of the location of label in each labeled-bearing peptide.

In the present invention's preferred embodiment, a protein such as a receptor, an antibody/antigen, an enzyme etc., is first labeled by allowing hydrogen exchange to occur between tritiated water and the protein. The binding partner to this protein, such as a substrate, cofactor, antibody/antigen, hapten, hormone, or membrane, is added to the protein and allowed to bind. The solution is changed to buffers free of heavy hydrogen, and the heavy hydrogens are allowed to be displaced by normal hydrogens in the water under conditions where the binding of the partners is unaffected. (According to Englander, participation in H-bonding is the principal impediment to the off-exchange of tritium). After the replacement is substantially finished, the complex may optionally be predigested to produce smaller bound fragments. This pre-digestion may be performed during the off exchange period. The solution conditions are then changed to minimize hydrogen exchange and the protein-binding partner complex is dissociated. The protein is then digested and analyzed to determine which of the amino acids is labeled. The analysis typically comprises a reverse phase HPLC separation of the peptide fragments. As each carboxy-terminal amino acid of the functionally labeled peptide is sequentially cleaved by the carboxypeptidase, the nitrogen which formed the slowly-exchanging peptide amide in the intact peptide bond is converted to a rapidly exchanging secondary amine, and any tritium label at that nitrogen is lost from the peptide within seconds, whereas all other amide bond tritium remain in place. The radioactivity of each subfragment sequentially generated by carboxypeptidase treatment of a given fragment is determined, permitting precise localization of the label.

In situ analysis of protein-binding partner interactions is possible, in vivo. The receptor protein, while present in its native environment as a component of an intact living cell, or as a component of a cellular secretion such as blood plasma, is on-exchanged by incubating cells or plasma in physiologic buffers supplemented with tritiated water. The binding partner is then added, allowed to complex to the cell or plasma-associated protein, and then off-exchange initiated by returning the cell or plasma to physiologic conditions free of tritiated water. During the off-exchange period the formed protein-binding partner complex is isolated from the cell or plasma by any purification procedure which allows the complex to remain continuously intact. At the end of the appropriate off-exchange period, fragmentation and analysis of purified complex proceeds as above.

In another embodiment, peptide amides on the receptor protein's surface are labeled by transfer of tritium that has been previously attached by proton exchange to the interaction surface of the binding partner. This procedure will functionally label receptor protein amides if they are slowed by complex formation and are also in intimate contact with the binding partner, in the complexed state. Amides that are distant from the interaction surface but slowed in exchange because of complex formation-induced allosteric changes in the protein will not be labeled.

BRIEF DESCRIPTION OF THE DRAWINGS

FIGS. 1a–1d depict the results of analysis (Panels A to D) of tritium associated with hemoglobin (Hgb) fragments produced by pepsin digestion of tritium-exchanged hemoglobin ±monoclonal, antibody followed by HPLC in $PO_4$ buffered solvents, pH 2.7. FIG. 1a: Absorbance (214 nM) tracing of unlabeled proteolyzed Hgb. FIG. 1b: Hgb on-exchanged for 4 hours, shifted to pH 2.7 and then proteolyzed without off exchange. FIG. 1c: Hgb on-exchanged for 4 hours, mixed with monoclonal β6 and then off-exchanged for 40 hours before proteolysis at pH 2.7. FIG. 1d: Hgb on-exchanged for 4 hours and then off-exchanged for 40 hours before proteolysis at pH 2.7.

FIGS. 4a–d depict the identification (Panels A to C) of hemoglobin peptides functionally labeled by interaction with haptoglobin.

FIG. 5a: β6 monoclonal interaction peptides; FIG. 5b: β121 monoclonal interaction peptides.

FIGS. 6a–e depict the results of carboxypeptidase P digestion of β1–14 peptide. Tritium-exchange-labeled synthetic β1–14 peptide was digested (0° C.) with carboxypeptidase-P (CP-P) using a range of enzyme concentrations and digestion times (indicated at far left margin). HPLC analysis as then performed as in FIG. 1a–d, but with simultaneous measurement of O.D.214 and radioactivity of column effluent. The positions of the several generated C-terminal truncated peptide fragments are indicated (numbers 3 through 9). Progressive generation of fragments is observed.

FIGS. 7a–e depict the results of reduction (Panels A to E) of disulfide bonds at pH 2.7. Tritium-exchange-labeled β1–14 peptide (2 µg at 0° C., pH 2.7) was supplemented with the peptide endothelin (4 µg), which contains two disulfide bonds (35), and the mixture incubated without FIG. 7a or with FIGS. 7b–e 50 mM Tris (2-carboxyethyl) phosphine (TCEP) for varying times at 0° C. FIGS. 7a, c–e, or 2 minutes at 22° C. FIG. 7b. The mixtures were then subjected to HPLC as in FIGS. 6a–e. The percent of endothelin that remained unreduced under each condition is indicated as is the fraction of tritium label that remained attached to the β1–14 peptide. Fifty percent reduction of endothelium disulfides is accomplished at pH 2.7 with an insignificant loss of peptide amide-bound tritium from the β1–14 peptide. "R" indicates the positions of reduced forms of endothelin.

DETAILED DESCRIPTION OF THE PREFERRED EMBODIMENTS

Figure 1A:
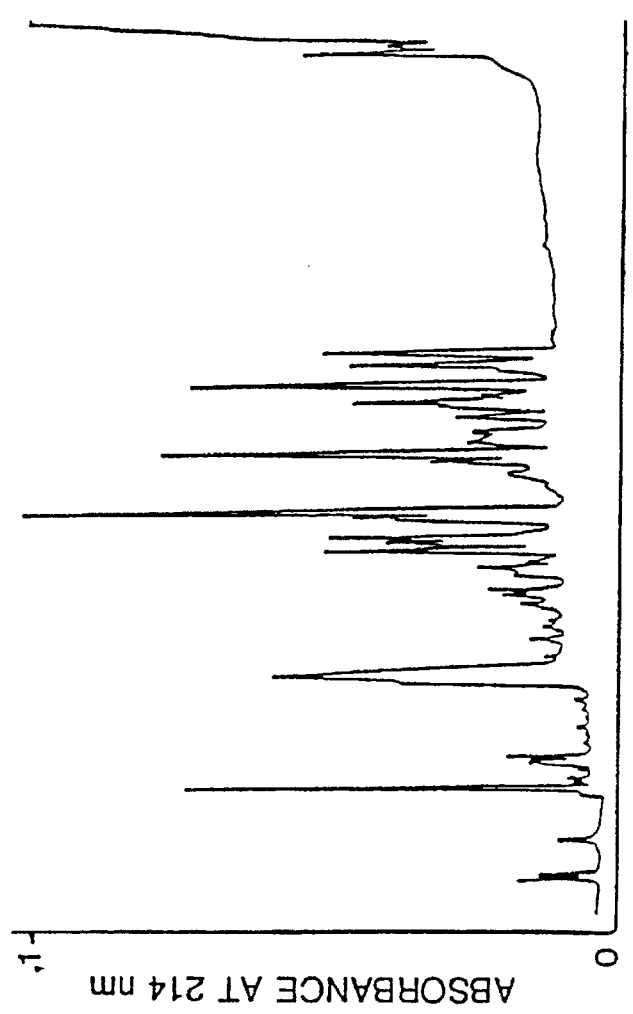

In one embodiment, the present invention contemplates the following procedure for characterization of a binding site:

A. The phenomenon of proton (tritium) exchange is used to substitute a radioactive probe (tritium) for each of the acidic protons (hydrogen) on the amino acids which make up the surface of the receptor protein, including the surface of the receptor's ligand binding site. This labelling is accomplished under essentially physiologic conditions by incubating the receptor protein in solutions containing tritiated water. (Preferably, the water is of high specific activity.)

B. Protein ligand (binding partner) is then added to the on-exchanged (tritiated) receptor protein and allowed to bind to its specific site on the receptor. Once the ligand has bound to the receptor, acidic protons on the amino acids which make up the surface of the receptor's binding site are no longer capable of efficiently interacting with the surrounding aqueous buffer, and further proton exchange is markedly inhibited.

C. The tritiated receptor-ligand complex is then transferred to physiologic buffers free of tritium. Tritium label on the receptor-ligand complex is allowed to exchange off the receptor. However, binding complex-dependent hydrogen-bonding between the protein and binding partner and limited solvent accessibility to the protein-binding partner interface in the complex are selective impediments to the off-exchange of peptide amide tritium label sandwiched between the protein and binding partner. After the removal (off-exchange) of tritium from other regions of the protein-binding partner complex is substantially finished, the result is the preferential retention of tritium label at the amides for which hydrogen exchange is slowed by virtue of protein-binding partner interactions, typically amides proximate to amino acids which make up the surface of the receptor's ligand binding site. Optionally, the complex may be subjected to limited proteolytic digestion, and/or disulfide reduction while off exchange is proceeding, as long as the integrity of the binding protein: binding partner interaction is not substantially perturbed by such maneuvers.

D. The specific peptide bond amides which bear the remaining tritium are then identified. This is done by:

(1) shifting the labeled receptor-ligand complex to conditions (e.g., 0°–40° C., pH 2.7) which dissociate the complex and at the same time slow down amide hydrogen exchange.

(2) subjecting the receptor to proteolysis followed by reverse phase (RP) high pressure liquid chromatographic (HPLC) separation (preferably 2-dimensional) of the resulting receptor fragments under continued slow proton exchange conditions. Receptor fragments bearing tritium label are identified, isolated, and characterized as to their amino acid sequence, and therefore their location within the primary amino acid sequence of the intact receptor.

(3) determining the location of tritium label within each peptide by subfragmenting the labeled peptides (e.g., with acid-reactive carboxypeptidases or tritium-exchange-compatible chemical methods) under slow proton exchange conditions and characterizing the labelled subfragments. For example, the identity of each of the several carboxy-terminus-truncated peptides is determined by amino acid analysis, peptide sequencing, or through the use of synthetic HPLC mobility marker peptides, and the amount of tritium label attached to each C-terminal truncated peptide determined by scintillation counting. In this manner, the precise location, within the protein, of each peptide amide that is functionally labeled with tritium by virtue of its interaction with binding partner is determined. Inferentially, in this manner, the precise amino acids which make up the surface of the receptor's binding site are then known. Studies may be performed to quantify the exchange rates of each of the labeled amides identified above both before and after complex formation with binding partner. This allows calculation of the magnitude of exchange slowing experienced by each of these amides consequent to complex formation, and allows optimization of on and off exchange times.

E. Parallel studies are performed in which the cognate binding partner is on-exchanged with tritium, complexed with receptor protein, off-exchanged as a binding partner-protein complex and slowed amides in the binding partner identified as above. This procedure results in the identification of the subregions of the binding partner which interact with the protein.

F. The knowledge of the identity of the precise contact peptides in both receptor and ligand is combined with additional structural information provided by the invention (identification of peptide amides of the protein and binding partner which are likely to directly form hydrogen bonds between protein and binding partner upon complex formation) to produce models for the complementary 3-dimensional structures of the receptor and ligand interaction surfaces. These models are then used as the basis of the design and production of appropriate peptide and peptidomimetic drugs.

The individual steps of this procedure will now be considered in greater detail.

1. On-Exchange

The protein under study is incubated in buffer supplemented with tritiated water ($^3H_2O$), preferably of high specific activity. This results in the time dependent reversible incorporation of tritium label into every peptide amide on the surface of the protein, including its (potential) ligand binding subregion, through the mechanism of proton exchange.

Any physiologic buffer appropriate for the interaction of the protein with its binding partner may be utilized (with no constraints imposed on buffer pH or temperature). Suitable buffers include phosphate buffered saline, 0.15 mM NaCl, 10 mM $PO_4$, pH 7.4 PBS. The use of small incubation volumes (0.1–10 μl) containing high concentrations of receptor protein (10–100 mg/ml) is preferred.

The necessary level of tritiation (and hence the concentration of tritium in the buffer) is dependent on the total amount of protein available for analysis. For analysis of protein, at least 10 Ci/ml is desirable; for 0.1 mg, 100 Ci/ml, and for 0.01 mg, 1000 Ci/ml. (Pure tritiated $H_2O$ is about 2500 Ci/ml.) For most applications, the tritiated water will be 50–500 Ci/ml. Without the use of these high specific activities, studies of proteins which are available in limited quantity would be much more difficult. (Even higher specific activity (e.g., 500–1,500 Ci/ml) may be used in the invention, but radiation safety considerations necessitate performance of such on- and off-exchange procedures in specialized facilities, such as are available in the tritium laboratory provided by the National Tritium Facility, Lawrence Berkeley Laboratories, University of California, Berkeley.)

It is not necessary that the tritium exchange analysis rely on only a single choice of "on-exchange" time. Rather, the skilled worker may carry out the experiment using a range of on-exchange times, preferably spanning several orders of magnitude (seconds to days) to allow selection of on-exchange times which allow efficient labeling of the various peptide amides present in the protein, which will become slowed in their exchange rate consequent to the interaction of the protein to its binding partner, and at the same time minimize background labeling of other amide positions after off-exchange is completed (see section 10 below).

2. Receptor-Binding Partner Complex Formation

After a suitable period of tritium on-exchange, the protein's binding partner is added to the tritiated protein-buffer solution and the two allowed to form a binding complex. The binding partner is preferably added in quantities sufficient to produce saturation binding to the protein (usually equimolar amounts) and at high concentrations (e.g., 10–100 mg/ml) to maximize the rate and extent of binding. To minimize tritium labeling of the added binding partner by proton exchange (important when utilizing short on-exchange times), $^3H_2O$ in the buffer is preferably diluted with tritium-free buffer (10–1000 fold dilution) within 0–100 seconds of binding partner addition. Additional manipulations detailed below may be used at this step to further minimize incorporation of tritium label into the binding partner.

3. Off-Exchange

The tritiated protein-binding partner complex is then transferred to physiologic buffers identical to those employed during on-exchange, but which are free of tritiated water. Tritium label on the protein then exchanges off the protein at rates identical to its on-exchange rate everywhere except at amides which have been slowed in their exchange rate by virtue of the interaction of protein with binding partner. With sufficient off-exchange time, the result is the specific retention of tritium label at each of the peptide amide bonds which occur between the amino acids which make up the surface of the protein's binding site for the binding partner. We refer to this process as a complex formation-dependent functional labeling of the protein with tritium. At least 90%, more preferably, at least 99%, of on-exchanged tritium label at other sites is off-exchanged from the protein.

In general, off-exchange is allowed to proceed for 5 to 50 times, more preferably about 10 times the on-exchange period, as this allows off-exchange from the protein of greater than 99% of the on-exchanged tritium label which has not experienced slowing of exchange rate subsequent to the protein's interaction with binding partner. Preliminary studies are performed with the protein and binding partner to determine the on and off exchange times which optimize the signal (tritium remaining in functionally labeled amides) to noise (tritium remaining in background amides) ratio (see section 8).

In preferred embodiments, the off-exchange procedure may be performed with the use of Sephadex G-25 spin columns prepared and utilized as described in Example 1 (below), by G25 column chromatography as described by Englander (6,19) or by use of perfusive HPLC supports that allow rapid separation of peptide/protein from solvent (Poros* columns, PerSeptive Biosystems, Boston, Mass.). The inventors have found that use of the G25 spin columns allows the separation of the complex from greater than 99.9% of buffer tritium. Residual buffer tritium and tritium off-exchanged from the complex may optionally be further removed by dialysis of the complex against tritium free buffer during off exchange.

Alternatively, complex formation and off-exchange can be accomplished by first reacting the on-exchanged protein-buffer mixture with binding partner which has been covalently attached to a solid support (e.g. binding-partner-Sepharose), allowing the on-exchanged protein to complex to the solid-phase binding partner, followed by washing of the sepharose-binding partner-protein conjugate with tritium free buffer. Alternatively, soluble protein-binding partner complexes may be formed as above, and captured with a solid phase adsorbent that can bind to either the protein or binding partner component of the complex Sepharose with covalently attached antibodies specific for protein or binding partner).

Most protein-ligand binding interactions that will be probed with this technique are reversible reactions: binding partner will dissociate from and rebind to the protein during the off-exchange period, and during the brief intervals where the protein's binding site is unoccupied with binding partner, proton off-exchange proceeds at the unprotected rate. It is therefore important to minimize the time that the binding site is unoccupied. In a preferred embodiment, this is accomplished by having both receptor and binding partner present at high concentration, e.g., at least mg/ml concentrations, up to 100 mg/ml concentrations each throughout the off-exchange period, and performing the on and off exchange reactions at temperatures at or below room temperature, preferably 4° C.

4. Predigestion of Functionally Labeled Protein-binding Partner Complex

During the off-exchange period, which typically lasts hours to days, the complex may optionally be chemically or enzymatically treated to produce the smallest fragment of protein which is still capable of remaining tightly bound to the binding partner, and this residual "trimmed" complex isolated. Removal of portions of the protein not essential for continued complex formation will decrease the number of background peptides generated during the subsequent acid proteolysis of the trimmed complex (Section 6). This pre-digestion and purification can be performed with a wide variety of proteases (e.g. trypsin, pronase, V-8 protease chymotrypsin proteinase-K) as well as certain chemical agents (e.g., cyanogen bromide, iodosobenzoic acid), and under virtually any conditions of induced partial protein denaturation (e.g. urea, guanidinium chloride sodium dodecyl sulfate, non-ionic detergents, reductants such as 2-mercaptoethanol, dithiothreitol), ionic strength, temperature, time and pH which do not substantially dissociate the contacting surfaces of the protein-binding partner complex. Excessive digestion efforts which result in dissociation of these surfaces from each other will cause a large fraction of functional tritium label to be immediately off-exchanged, as greater than 50% of peptide amides in the dissociating surfaces will have exchange half-lives of less than 1 minute at pH approximately 7. The goal is to generate and isolate a fragment of the protein, preferably 15–100 kD in size more preferably 15 kD, which remains attached to the binding partner. Often "ligand stabilization" of proteins which are proteolysed while bound to binding partner allows the continued binding of the protein fragments to partner.

Preliminary studies may be performed with the off-exchanged complex to determine conditions which result in a suitably trimmed protein-binding partner complex. In a preferred embodiment, the quantity of residual tritium functionally bound to the intact off-exchanged complex is first determined by measurement of tritium which migrates with the void volume (Mr >10,000 kD) on a G25 spin column (pH 7.4). Aliquots of the complex are then subjected to varied fragmentation conditions, and the fraction of tritium label which remains attached to polypeptides under each digestion condition (migrates with G25 void volume) determined. The proteolytic products of the most vigorous digestions which "release" less than 5% of complex-associated tritium are (as per Section 5) adjusted to pH 2.7, 0° C., subjected to RP-HPLC at pH 2.7, 0° C., and peptides/protein fragments which bear label identified, isolated, and their molecular weights determined by SDS-PAGE. The labeled proteolytic products produced in these limited digests are likely to be large polypeptides, and therefore RP-HPLC supports suitable to the purification of such peptides (C-4, phenyl columns) are utilized. Alternatively, when solid-phase adsorbents are used for complex formation/off-exchange (step 3), proteolysis as above, now of the solid phase binding partner-protein complex, is allowed to proceed as extensively as possible without release from the solid support of greater than 5% functionally attached tritium. The predigested protein/complex is then released from the immunoadsorbent with denaturants including a shift to pH 2.7, and the predigested protein further proteolysed with pepsin other acid reactive proteases.

5. Switch to Slow Amide Proton Exchange Conditions

The protein-binding partner complex (or predigested complex—see Step 4) is then shifted to conditions of temperature and pH which greatly slow the half life of peptide amide proton exchange, dissociate the complex, and essentially "freezes" in place the protein binding site-retained tritium label. In a preferred embodiment, the complex is shifted to 0° C., and pH 2.7 conditions under which the half life of exchange of peptide-amide label in fully denatured peptides is at least 70 minutes. The label will be sufficiently held in place under these conditions so that several rounds of proteolytic fragmentation, HPLC separation, and tritium quantification can be performed without unacceptable loss of label.

5A. Disruption of Protein Disulfide Bonds under Acidic Conditions

High resolution localization of tritium label-bearing amides requires the proteolytic generation of peptides less than approximately 15–20 amino acids in size under conditions which allow the label to remain in place (0° C., pH 2.7). The ability of any protease to fragment a protein or peptide is limited by the accessibility of the protease to susceptible peptide bonds. While denaturants such as acidic pH, urea, detergents, and organic co-solvents can partially denature proteins and expose many otherwise structurally shielded peptide bonds, pre-existing disulfide bonds within a protein can prevent sufficient denaturation with these agents alone. In conventional protein structural studies, disulfides are usually cleaved by reduction with 2-mercaptoethanol, dithiothreitol, and other reductants which unfortunately require a pH greater than 6 and elevated temperature for sufficient activity, and are therefore not useful for the reduction of disulfides at pH 2.7 or below. For this reason, the tritium exchange art has not attempted any form of disulfide bond disruption, has been restricted to the study of proteins without intrinsic disulfide bonds, and has accepted the low resolution achievable without disulfide bond disruption. The applicants have recognized and demonstrated that acid-reactive phosphines such as Tris (2-carboxyethyl) phosphine (TCEP) (31–36) can be used to disrupt disulfides under the acidic pH and low temperature constraints required for tritium exchange analysis (see FIGS. 7a–e). We have established that these manipulations disrupt these associations and at the same time continue to produce a markedly slowed proton exchange rate for peptide amide protons.

6. Generation of Tritium-Labeled Peptide Fragments and Purification by Two-Dimensional RP-HPLC The denatured and disulfide-disrupted protein-binding protein mixture is then subjected to acid proteolysis with high concentrations of a protease which is stable and active with the aforementioned conditions (e.g., pH 2.7, 0° C.). Suitable proteases include pepsin (19), cathepsin-D (37) Aspergillus proteases (37a–37c), thermolysin (38) and mixtures of these proteases. In a preferred embodiment, pepsin is used, preferably at a concentration of 10 mg/ml pepsin at 0° C. pH 2.7 for 5–30 minutes, preferably 10 minutes.

Applicants have found that RP-HPLC resolution of co-migrating multiple peptides is greatly improved by resorting to a two-dimensional RP-HPLC separation in which two sequential HPLC separations are performed at substantially different pH's, e.g. 2.7 and 2.1; proteolytic digests are first separated at pH 2.7 in phosphate buffered solvents and each eluted peptide peak fraction which contains tritium-labeled amides is identified, collected, and then subjected to a second HPLC separation performed in trifluoracidic acid (TFA)-buffered solvents at pH 2.1.

To precisely localize the protein's amides which are functionally labeled with tritium, small peptides bearing the retained tritium label (preferably, 5–25 amino acids in size) must be proteolytically generated from labeled protein and separated from the many other unlabeled peptides generated by fragmentation of the protein, all under conditions which minimize off-exchange of amide tritium from the peptide. Small peptides have little secondary structure and therefore their amides are free to exchange with solvent hydrogen. If tritium label is to remain in place on such peptides, proteolysis and RP-HPLC conditions must be adjusted to slow such off-exchange.

Englander (6) reported that at 0° C., the tritium label present on the amides of small unfolded peptides was most stable (slow to off-exchange) at pH 2.7, and at the rate of off-exchange increase rapidly (10 fold per pH unit) as one moved away from that pH. Based on these studies, Englander and others have exclusively employed a single HPLC separation step performed at pH 2.7. This pH constraint requires that acid proteases be utilized for tritium labeled protein fragmentation.

As acid proteases in general have very broad cleavage specificity, they fragment the protein into a very large number of different peptides. In most protein-binding partner systems studied by tritium exchange, it is likely that the interacting binding surfaces will contain roughly 10–20 tritium labeled peptide amide which upon proteolysis will result in approximately 1–5 label-bearing peptides, the precise number depending on the inherent fragmentation mode of the protein under study with the proteases utilized. The number of "background," non-labeled peptides (derived from regions of the protein and binding partner that do not participate in the binding interaction) generated by the fragmentation procedure will be a direct function of the size of the protein. Background peptides will be present in the proteolytic digest in numbers 10–1,000 times greater than will be functionally labeled peptides when proteins with sizes in the range of 30–200 kD are proteolyzed.

This large number of background peptides causes two difficulties: First, they must all be cleanly separated from the functionally labeled peptides to allow microsequence analysis and identification of the label-bearing peptides. Second, background peptides contain small amounts of tritium label and even though the amount of label per background peptide is generally less than 1% of that of functionally labeled peptides, background peptides are present in much greater amounts and are likely to obscure the presence of functionally labeled peptides and analytical separation.

Given these considerations, only proteins less than 30 kD in size have been successfully characterized by medium resolution tritium exchange. Upon acid proteolysis of larger proteins, so many different fragments would be obtained that individual fractions obtained on a single HPLC separation performed at pH 2.7 would be unacceptably contaminated with background peptides.

Figure 6D:
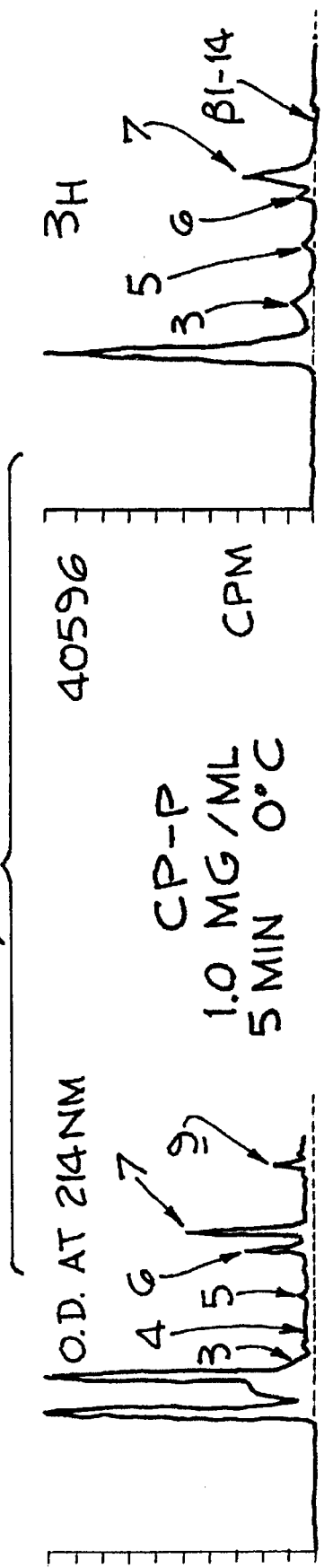
Figure 6E:
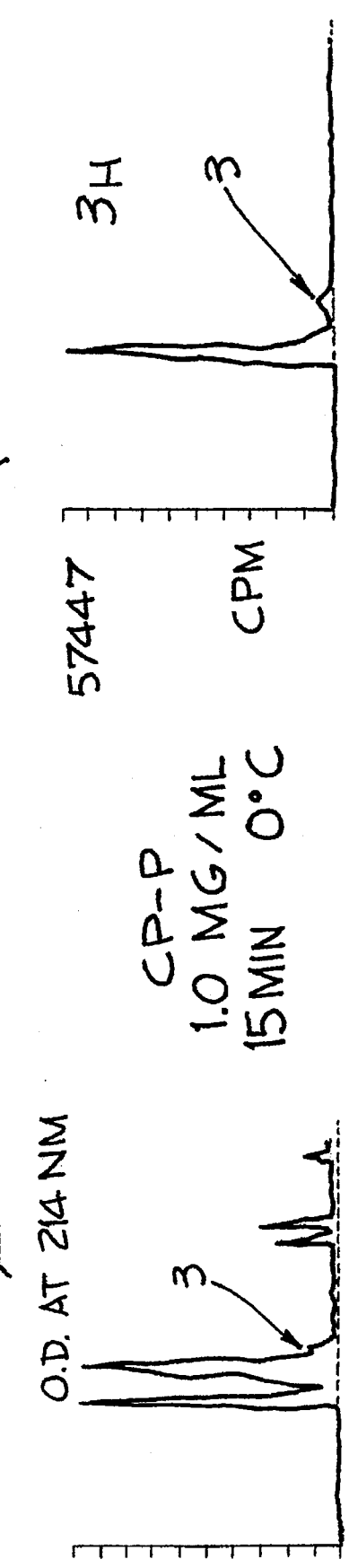
Figure 7D:
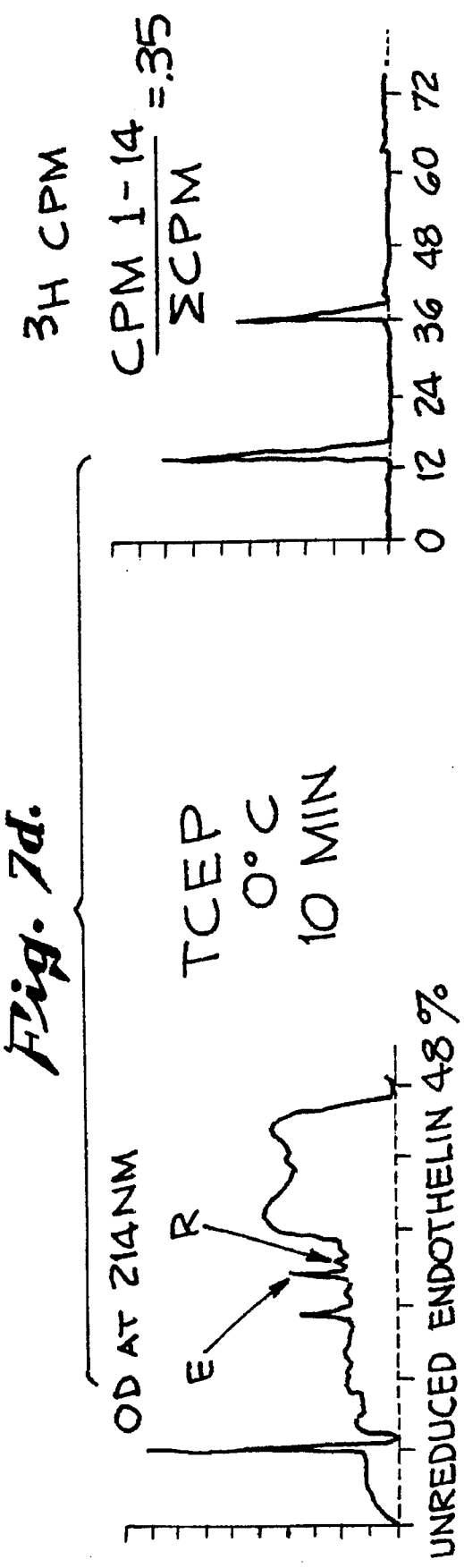
Figure 7E:
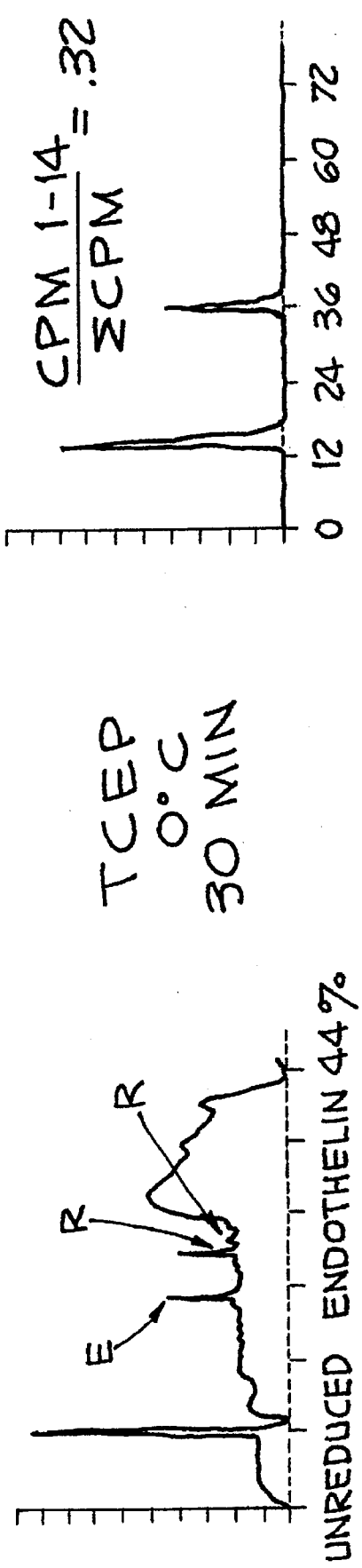

Applicant has discovered that the art has overstated the sensitivity of tritium exchange-labeled peptides to pH in RP-HPLC separation. Surprisingly, applicant has found that at 0° C., tritium's attachment to peptide is sufficiently stable as to permit analysis in HPLC solvent buffered with 0.1–0.115% trifluroacetic acid (TFA) which has a pH of 2.1 (see FIG. 6). While the acceptable pH range will vary with the choice of nonaqueous polar co-solvent (the optimal pH increases if a polar nonaqueous solvent is introduced), the fact remains that the pH acceptable for RP-HPLC analysis of small peptides was previously considered to be essentially fixed, limiting the separation of amide-labeled peptides within a proteolytic digest to that achievable with a single HPLC column run performed at pH 2.7. Since the applicants have found the tritium label is operationally stable over a broader pH range, it is possible to depart from Englander's recommended pH seeking HPLC conditions which result in more effective separation of the peptide fragments, for example, a two-dimensional separation at different pHs.

In a preferred embodiment of the invention, digested, tritium-labeled protein fragments are first separated by means capable of sufficiently resolving the fragments, such as by RP-HPLC (utilizing a number of potential chromatographic support including C4, C18, phenol and ion exchange, preferably C18). This separation may be performed at pH 2.1–3.5 and 4°–0° C., more preferably, at pH 2.7 and 0° C., which may accomplished by employment of any buffer systems which operate at this pH, including citrate, chloride; acetate, more preferably phosphate. Peptides are eluted from the reverse phase column with a similarly buffered gradient of polar co-solvents including methanol, dioxane, propanol, more preferably acetonitrile. Eluted peptides are detected by on-line ultraviolet light absorption spectroscopy performed at frequencies between 200 and 300 nM, preferably 214 nM. Tritium label is detected by scintillation counting of a sampled fraction of the HPLC column affluent. Peptides bearing label that has been specifically protected from off-exchange by complex formation with binding partner are identified by comparing the specific activity of each labeled peptide to the specific activity of the same peptide prepared from protein subjected to identical on/off exchange, proteolysis and HPLC conditions, but which have been off-exchanged without added binding partner.

HPLC fractions containing peptides with such functionally labeled amides are then subjected to a second dimension RP-HPLC separation which may be performed at pH 2.1–3.5 and 4°–0° C., more preferably, at pH 2.1 and 0° C., accompanied by any buffer systems which operates at this pH, including citrate, chloride, acetate, phosphate, more preferably TFA (0.1–0.115%). Peptides are eluted from their reverse phase column with a similarly buffered gradient of polar co-solvents including methanol, dioxane, propanol, more preferably acetonitrile. Eluted peptides are detected, tritium measured and functionally labeled peptides identified as in the first HPLC dimension described above. Functionally labeled peptides are isolated (collection of the appropriate fraction of column effluent), water, acetonitrile, and TFA removed by evaporation, and the remaining purified peptides each characterized as to its primary amino acid structure by conventional techniques, e.g., amino acid analysis of complete acid hydrolysates or gas-phase Edman degradation microsequencing. Reference is then made to the previously known amino acid sequence of the intact protein to infer the location of the tritium-labeled peptides within the intact protein's primary sequence. Employment of TFA buffer in the second dimension has the additional advantage that no residual salt (i.e. phosphate) remains after solvent evaporation. Residual phosphate frequently interferes with the chemical reactions required for amino acid analysis and edman degradation, a problem obviated by the use of TFA use of volatile TFA in the second dimension buffer.

7. High Resolution Sublocalization of Labeled Amides within Label-Bearing Peptides To routinely localize peptide amide tritium label to the single amino acid level, the applicants systematically cleave every peptide bond within a purified label-bearing peptide. Acidic conditions must be used for this proteolysis as the small peptides generated have no stable conformational structure and rapid loss of tritium label from the amides would occur if rates of exchange were not slowed by ambient acidic pH. However, most known acid-reactive proteases cleave peptides in a basically nonspecific manner similar to that of pepsin; studies employing other pepsin-like proteases have not proved to be of significant utility in increasing resolution of labeled amides.

The applicants have recognized that a special class of acid-reactive proteases, the carboxypeptidases, are able to generate all required subfragments of pepsin-generated peptides in quantities sufficient for high resolution tritium localization. Many carboxypeptidases are active at pH 2.7 and sequentially cleave amino acids from the carboxy terminus of peptides. Such enzymes include carboxypeptidase P, Y, W, and C (39). While carboxypeptidases have been used for limited carboxy-terminal sequencing of peptides, often at pH in the range of 2.7 their use in tritium exchange techniques has not been disclosed. The need to minimize tritium losses forbids the use of carboxypeptidases which are inactive in acidic (pH 2.7) buffers, such as carboxypeptidases A and B. However, carboxypeptidase-P, Y, and several other acid-reactive carboxypeptidases (W,C) are suitable for proteolysis of peptides under acidic conditions (39). While the inventors recognized that carboxypeptidases would be of great utility to tritium exchange studies, the tritium exchange art has failed to recognize this for 20 years, perhaps, because the carboxypeptidases are even more non-specific in the types of peptide bonds they cleave then pepsin-like proteases and therefore might have been thought to result in inadequate recovery of any single subpeptide.

Furthermore, chemical procedures employing pentafluoropropionic anhydride can produce sets of C-terminal-truncated peptide fragments under slowed amide exchange conditions (see below, 41,42).

In the preferred embodiment, tritium-exchange-labeled proteins are nonspecifically fragmented with pepsin or pepsin-like proteases, the resulting tritium-labeled peptides isolated by two-dimensional HPLC and these in turn exhaustively subfragmented by controlled, step-wise digestion with acid-reactive carboxypeptidases and/or by chemical means (see below). These digests are then analyzed on RP-HPLC performed at 0° C. in TFA-containing buffers (pH 2.1) and each of the generated subfragments (typically 5–20) is then identified as to its structure and content of tritium label and label thereby assigned to specific peptide amide positions. This procedure was not used or proposed in any of the prior art to further sublocalize the labelling sites, though improved resolution was certainly a goal of the art. The closest the tritium exchange art comes is Englander's general suggestion that further fragmentations with another "acid protease" might be useful, and disclosure of essentially unsuccessful enhancements by use of two additional pepsin-like proteases.

The inventors have recognized that controlled sequential carboxy-terminal digestion of tritium-labeled peptides with carboxypeptidases can be performed under conditions which result in the production of analytically sufficient quantities of a set of carboxy-terminal truncated daughter peptides each shorter than the preceding one by a single carboxy-terminal amino acid. As each carboxy-terminal amino acid of the functionally labeled peptide is sequentially cleaved by the carboxypeptidase, the nitrogen which formed the slow-exchanging peptide amide in the intact peptide bond is converted to a rapidly exchanging secondary amine, and any tritium label at that nitrogen is lost from the peptide within seconds, even at acidic pH. A difference in the molar quantity of tritium label associated with any two sequential subpeptides implies that label is localized at the peptide bond amide which differs between the two subpeptides.

In a preferred embodiment, synthetic peptides are produced (by standard peptide synthesis techniques) that are identical in primary amino acid sequence to each of the functionally labeled pepsin-generated peptides identified in Step 6. The synthetic peptides may then be used in preliminary carboxypeptidase digestion (pH 2.7, 0° C.) and HPLC (in TFA-buffered solvents) studies to determine; 1) the optimal conditions of digestion time and protease concentration which result in the production and identification digestion on all possible carboxypeptidase products of the peptide under study; and 2) the HPLC elution position (mobility) of each carboxypeptidase-generated subfragment of synthetic peptide.

To facilitate this latter procedure, a set of synthetic peptides may be produced consisting of all possible carboxy-terminal truncated daughter peptides which an acid carboxypeptidase could produce upon digestion of a "parent" peptide. These serve as HPLC mobility identity standards and allow the deduction of the identity of daughter peptides actually generated by carboxypeptidase digestion. Certain daughter peptides may be enzymatically produced in quantities insufficient for direct amino acid analysis or sequencing, but their HPLC mobility can be measured and compared to that of the synthetic peptides. Peptides can be detected and quantified by standard in-line spectrophotometers (typically UV absorbance at 200–214 nM) at levels well below the amounts needed for amino acid analysis or gas-phase Edman sequencing.

After these preliminary studies, the pepsin-generated HPLC isolated, functionally labeled peptide (prepared in Step 6) is then carboxypeptidase digested and analyzed under the foregoing experimentally optimized conditions, the identity of each fragment determined (by peptide sequencing or by reference to the mobility of synthetic peptide mobility marker) and the amount of tritium associated with each peptide subfragment determined.

Alternatively, a chemical technique may be used for the successive carboxy terminal degradation of peptides under slowed tritium exchange conditions. Tritium-labeled peptides in HPLC buffers are held at −35° C. and solvents removed by cryosublimation (40a, 40b; vacuum at 1–20 millitorr, solvents collected in a liquid nitrogen trap). The dried peptide is then reacted with vapor phase pentafluoropropionic acid anhydride (PFPA) as described in (54,55) except that the peptide temperature is kept at −35° C. for times up to 3 hours. PFPA is then removed by vacuum and the fragmented peptide made to 50 mM $PO_4$ pH2.7, and analyzed by HPLC.

8. Optimization of On and Off Exchange Times

Each peptide amide hydrogen associated with the protein-binding partner interaction surface has a unique exchange rate with solvent tritium in the native, unliganded state, which is then shifted to another distinct exchange rate once protein-binding partner complex formation has occurred. The signal to noise ratio (ratio of tritium functionally bound to this peptide amide over total background tritium bound to all other peptide amides in the protein) can be optimized by a knowledge of the exchange rates of this amide hydrogen in the native unliganded protein and in the protein-binding partner complex.

An amide hydrogen with an exchange half-life of one minute in the protein's native, unliganded state and 10 minutes in the liganded state might be optimally studied by on-exchanging the receptor protein for 2 minutes (2 half-lives of on-exchange time will result in incorporation of tritium at 75% of the maximal possible equilibrium labeling of the peptide amide) followed by 10 minutes of off-exchange in the liganded state (50% of on-exchanged label will remain on the functionally labeled peptide amide and less than 0.1% of on-exchanged label will remain on each of the background labeled peptide amides).

To measure the exchange rates of a particular functionally labelable peptide amide as it exists in the native, unliganded protein, aliquots of protein are on-exchanged for varying times (0.5 seconds to 24 hours), bound to binding partner, and then off-exchanged for a fixed time, preferably 24 hours. After pH 2.7, 0° C. proteolytic digestion and HPLC separation, radioactivity associated with the peptide fragment containing the peptide amide under study is measured. The amount of the radioactivity which represents background (amides which are not functionally labeled) is determined by measuring the amount of label associated with the same peptide when the protein is on-exchanged for the same duration but off-exchanged for 24 hours in the absence of added ligand prior to proteolysis and HPLC analysis. Specific radioactivity associated with the amide is determined as a function of on-exchange time, and the half-life of (on) exchange of the amide in the unliganded protein calculated.

To determine the exchange rate of the same peptide amide when it is in the protein-binding partner complex, protein is on-exchanged for a fixed, long period of time (preferably 24 hrs) complexed with binding partner, off-exchanged for varying times (preferably 10 seconds to 4 days), acid proteolysed, and HPLC analyzed as above. Specific radioactivity associated with the amide is determined as a function of off-exchange time, and the half-life of (off)-exchange of the amide in the liganded protein calculated. With this information the times of on and off-exchange are adjusted to optimize the signal/noise ratio for each of the amides functionally labeled in the protein-binding partner system under study.

9. Modeling of Receptor-Ligand Contact Surfaces

Studies identical in design to those described above (1–8) may also be performed on the corresponding binding partner protein (the binding partner protein is on-exchanged, liganded to receptor protein, off-exchanged, etc.), resulting in the identification of the amides of the binding partner which are slowed in exchange by virtue of interaction with receptor protein. The knowledge of the identity of the precise contact peptides in both protein and binding partner may be used to produce computer-assisted models for the complementary 3-dimensional structures of the protein and binding partner surfaces.

Construction of these models is aided by additional information provided by the invention which allows the identification of a subset of peptide amides on the protein's binding surface which are likely to form hydrogen bonds with acceptor residues on the cognate binding protein contact surface. While most of the peptide amides present on the native, uncomplexed protein or binding partner interaction surfaces can be expected to be hydrogen bonded to other portions of the same protein, a fraction of these peptide amides, possibly approaching 50%, may be hydrogen bonded only to solvent. As most protein-binding partner contact surfaces are highly complementary to each other, it is likely that upon complex formation solvent water is removed from the interaction surfaces, and amides previously hydrogen bonded to water will form new hydrogen bonds to the complementary surface of the partner. This subset of binding surface amides is readily identified in our studies (Step 8) as they will have an exchange rate in the protein's native, unliganded state of 0.5 seconds at pH 7.0 and 0° C. These amides can form hydrogen bonds with the complementary surface only if their hydrogens are oriented in the direction of the complementary surface. This in turn places orientation constraints on the entire associated peptide bond and to a lesser degree the side chains of the two flanking amino acid residues of each such amide. Application of these constraints to the foregoing models of interaction surface structure allow higher resolution modeling of the 3-dimensional structure of the protein-binding partner ligand interaction surfaces.

10. Automation of the Procedures Required for the Performance of Enzymatic Degradation and HPLC Analysis under Slowed Tritium Exchange Conditions While digestion and analysis procedures are performed at 0° C., analytical samples of tritium exchange-labeled peptides must be stored at temperatures of approximately −60° to −80° C. if unacceptable losses of label from the peptide are to be avoided over intervals of hours to weeks. Tritium exchange continues in frozen samples in a manner inversely related to temperature but effectively stops at temperatures of approximately −70° C. At present, tritium exchange analysis is performed by manually removing samples from −70° C. storage, melting them manually at 0° C., manual addition of reagents (buffers, enzymes) and manual injection of samples onto the HPLC column. These manipulations are labor intensive and expose the samples to inadvertent heating during handling. If HPLC-separated peptides are to be collected and stored for future study, they are manually collected and stored at −70° C. No presently available robotic HPLC autosampler has the capability of performing the necessary manipulations on samples stored in the frozen state.

We have modified a Spectraphysics AS3000® autosampler so as to allow automation of these steps. These modifications were: inclusion of a solid dry ice bath in which samples are stored until analysis; use of modified fluidic syringes which operate reliably at 0° C.; control of the autosampler by an external computer; and placement of the autosampler HPLC column and spectrophotometer within a 0° C. refrigerator. Under computerized control, the autosampler's mechanical arm lifts the desired sample from the −70° C. bath, and places it in a heater/mixer which rapidly melts the sample at 0° C. The liquified sample is then automatically injected onto the HPLC column. Operation of HPLC pumps, on-line radiation counter and data acquisition is similarly automated.

To collect tritium-labeled, HPLC-separated peptides under slowed exchange conditions, a Gilson-303® fraction collector (also present in the 0° C. refrigerator) has been modified so that the sample collection tubes are immersed in a dry ice bath. Computer-directed diversion of desired HPLC effluent fractions into these prechilled tubes results in rapid freezing of the desired tritium-labeled peptides to −70° C.

Additional Embodiments a. Fast atom bombardment tandem mass 'spectroscopy (FAB MS:MS): This modality may also be employed for the precise localization of functionally-exchanged label within label-bearing peptides. FAB or electrospray MS:MS has become a standard technology by which the amino acid sequence of proteolytically generated peptides can be rapidly determined (43). It is commonly used to study peptides which contain amino acids which have been deuterated at carbon-hydrogen positions, and thereby determine the precise location of the deuterated amino acid within the peptide's primary sequence. This is possible because mass spectroscopic techniques can detect the slight increase in a particular amino acid's molecular weight due to the heavier mass of deuterium. McCloskey, et al (44) discloses use of deuterium exchange of proteins to study conformational changes by mass spectrometry.

The applicants have devised a proton-exchange technique identical to the one described in sections 1–5 above except that on-exchange is performed in deuterated water (preferably 80–99% mole fraction deuterated water, more preferably 98% mole fraction deuterated water) supplemented with 2% mole fraction tritiated water (e.g., 50 Ci/ml). This modified procedure, after addition of binding partner and off-exchange specifically labels, both with exchanged deuterium (at equilibrium, 98% mole fraction) and tritium (to the same specific activity as in the standard procedure), the peptide amides which make up the interaction surface between protein and binding partner. Proteolytically generated fragments of protein functionally labeled with deuterium and tritium are identified (by following tritium on dimensional HPLC analysis as in Step 6) isolated, and then subjected to FAB or electrospray MS:MS under conditions in which the deuterium remains in place on the functionally labeled peptide amides. The applicants have recognized that standard peptide sequence analysis FAB MS:MS (in which extensive collision-induced fragmentation of peptides induced techniques can be performed under conditions which minimize peptide amide proton exchange: samples can be maintained at 4° C. to zero degrees C. with the use of a refrigerated sample introduction probe; samples can be introduced in buffers which range in pH between 1 and 3; and analyses are completed in a matter of minutes.

In a preferred embodiment, receptor-binding partner complexes functionally labeled with deuterium and tritium at their interaction surface are (under slowed exchanged conditions as described above for high resolution tritium exchange analysis) are pepsin digested, subjected to rpHPLC in 0.1% TFA-containing buffers and column effluent containing labeled peptides subjected to FAB:MS utilizing either single sample injection, or continuous flow techniques. Molecular ions of the peptides are generated and isolated in the first mass spectrometer, subjected collision-induced fragmentation in an adjoining collision chamber, and the resulting fragments separated and molecular weights (M/Z) determined in the second linked mass spectrometer. Peptide fragments which bear functionally attached deuterium are identified by an increase in their molecular weight of one atomic unit when compared to the same peptide fragment generated from undeuterated receptor-binding partner. Sufficient subfragmentation and analysis as above results in the deduction of the specific location of functionally-bound deuterium within each pepsin generated, deuterium-bearing peptide. Alternatively, single stage Fab mass spectrometry can be performed on label-bearing, pepsin generated peptides, that are progressively digested in situ on the mass spectrometer Fab probe tip (under slowed exchange conditions) with acid-reactive carboxypeptidases (41). As digestion proceeds, molecular ions of each of the resulting enzyme-generated carboxy-terminal truncated peptide subfragments is detected by the mass spectrometer, and its molecular weight compared to that known for the undeuterated form of the same peptide fragment.

b. Tritium exchange analysis of protein-binding partner complexes which are experimentally formed in situ.

Tritium exchange analysis may be conducted of the contacting surfaces of protein-binding partner complexes which are experimentally formed in situ. The protein, while present in its native environment as a component of an intact living cell, or as a component of a cellular secretion such as blood plasma, is on-exchanged by incubating cells or plasma in physiologic buffers supplemented with tritiated water. The binding partner is then added, allowed to complex to the cell or plasma-associated protein, and then off-exchange initiated by returning the cell or plasma to physiologic conditions free of tritiated water. During the off-exchange period (hours to days) the formed protein-binding partner complex is isolated from the cell or plasma by any purification procedure which allows the complex to remain continuously intact. At the end of the appropriate off-exchange period, fragmentation and analysis of purified complex proceeds as above.

c. Labeling of receptor protein binding site amides by transfer to the receptor interaction surface of tritium previously attached by proton exchange to the interaction surface of the binding partner.

This procedure will functionally label receptor protein amides if they are slowed by complex formation and are also in intimate contact with the binding partner in the complexed state. Receptor protein amides that are slowed because of complex formation-induced allosteric changes in regions of the protein which are not near the protein-binding partner interaction surface will not be labeled. This procedure may be performed as follows:

1) binding partner is added to physiologic buffers containing high specific activity tritiated water to initiate tritium exchange labeling of the binding partner;

2) After sufficient labeling is achieved, binding partner is separated from the vast excess of solvent tritium under conditions which produce minimal loss of tritium label from the binding partner. This can be accomplished by: a) shifting the buffer conditions to those of slowed exchange (0° C., acidic pH) followed by G-25 spin column separation of the binding partner into tritium-free buffer or b) employing stopped-flow techniques in which the on-exchange mixture is rapidly diluted with large volumes of tritium free buffer;

3) the tritium-labeled binding partner, now free of excess solvent tritium, is added to receptor protein and buffer conditions adjusted to allow complex formation to take place between the two under physiologic conditions (room temperature, pH 7);

4) The complex is then incubated for periods of time sufficient to allow transfer of tritium label from the labeled binding partner to the receptor protein. During this incubation period, tritium which has on-exchanged to regions of the binding partner that are distant from the receptor-binding partner interaction surface will leave the binding partner by exchange with solvent hydrogen and be rapidly diluted in the large volume of solvent water. Tritium label that has been attached to the portion of the binding partner which subsequently interacts with receptor protein will be capable of exchanging from the binding partner only during the brief intervals when receptor protein is dissociated (separated) from binding partner at the molecular level. The result will be the progressive transfer of a portion of the tritium from the binding partner interaction surface to exchangeable amides on the cognate receptor protein interaction surface;

5) After an incubation period that maximizes tritium transfer, the complex is proteolytically digested and fragments of receptor protein that bear tritium label are identified, and further characterized as in foregoing sections 4–7.

EXAMPLES

As a demonstration of the practical use of this technology, we have studied the interaction of human hemoglobin with two different monoclonal antibodies known to be reactive with defined and previously identified subregions of the hemoglobin binding protein haptoglobin. For these studies, we employed monoclonal antibody $\beta^6$-1-23456 (specific for the human hemoglobin $\beta$ chain; epitope centered on or about $\beta$6Glu and monoclonal antibody $\beta^{121}$ (specific for the human hemoglobin $\beta$ chain in the region of residue $\beta$121), both antibodies being the generous gift of C. R. Kiefer, Medical College of Georgia, Augusta, Ga. (51). Human haptoglobin was obtained from Calbiochem Corporation, La Jolla, Calif.

Preparation of hemoglobin: Blood was drawn from a normal donor into sodium heparin at 10 U/ml. Red blood cells were washed five times in cold phosphate buffered saline (PBS) (pH 7.4) with the buffy coat aspirated after each wash. An equal volume cold distilled water was added to the washed cell pellet to lyse cells, and then a one-half volume of cold toluene was added with vigorous vortexing. This mixture was centrifuged for 30 minutes in a cold Sorvall* centrifuge (Dupont) rotor at 15,000 rpm (33,000× g). The hemoglobin (middle) layer was removed and the centrifugation and hemoglobin decantation repeated. The isolated hemoglobin was dialyzed against four changes of cold 0.1M sodium phosphate, 0.5% NaCl pH 7.4. After dialysis, the sample was treated with carbon monoxide for 15 minutes. Final hemoglobin concentration was measured by using a molar extinction for heme at 540 nm of 14,270. The preparation was stored frozen in aliquots at −70° C.

Preparation of pepsin: Porcine pepsin (Worthington Biochemical Corp.) was dissolved at 10 mg/ml in 50 mM sodium acetate pH 4.5 and dialyzed against the same solution to remove proteolytic fragments. It was stored frozen in aliquots at 70° C.

Tritium exchange: All steps were performed at 0° C. On-exchange was initiated by mixing equal volumes (5 μl) of isolated hemoglobin (300 mg/ml) and tritiated water (50 Ci/ml) and the mixture incubated for four hours. Aliquots of this mixture (1.3 μl) were then added to equimolar quantities of either monoclonal $\beta^6$, monoclonal $\beta^{121}$, haptoglobin, (all at 10 mg/ml in PBS, pH 7.4, in a final incubation volume of 75 μl) or added to 75 μl of PBS alone. These hemoglobin-ligand mixtures were then immediately applied to 2 ml Sephadex* G-25 spin columns and centrifuged minutes at 1100× g. Spin columns were prepared by filling 3 ml polypropylene columns (Fisher Scientific) with 2 ml of Sephadex G-25 fine equilibrated in PBS pH 7.4 plus 0.1% Triton* X-100. Columns were pre-spun at 1100× g for 2 minutes just before use. After column separation, samples were off-exchanged by incubation for a period of 40 hours, ten times the length of on-exchange. Samples were then hydrolyzed with pepsin. Typically, 25 μl of off-exchanged mixture containing 70 μg of hemoglobin was added to 10 μg pepsin in 110 μl of 0.1M NaPO$_4$ pH 2.7 plus 2.5 μl 0.5M H$_3$PO$_4$, the mixture incubated on ice for 10 minutes and then injected onto the HPLC column. An aliquot of on-exchanged hemoglobin was immediately adjusted to pH 2.7, passed over a pH 2.7 (0.1M NAPO4 pH 2.7) also proteolyzed and analyzed as above without a period of off-exchange. To measure on-exchange rates of specifically labeled amide protons, hemoglobin was on-exchanged as above but with time intervals ranging from 10 sec–18 hours, reacted with ligand, and off-exchanged for 18 hours. Samples were then proteolyzed, subjected to HPLC as below, and specific label on peptides quantified as a function of on-exchange time.

High pressure liquid chromatography: Digested samples were analyzed on a Waters HPLC unit modified by putting the column and injector under melting ice. Mobile phase was prepared using Barnstead nanopure water, Aldrich ultrapure sodium phosphate, J.T. Baker ultrex* grade HCL and HPLC grade acetonitrile from Burdick & Jackson. Mobile phase consisted of 50 mM NaPO$_4$ pH 2.7 (solvent A) and a mixture of 20% 50 mM NaPO$_4$ and 80% acetonitrile (ACN) final pH 2.7 (solvent B). Separation of peptides was achieved using a 30 cm Phenomenex Bondclone* 10 C18 column. The gradient program started at 100% A 0% B and altered the client to 83%A, 17%B over 3.4 minutes. From 3.4 to 6.7 minutes the system ran at a constant 83%A, 17%B and from 6.7 to 73.3 minutes the program implemented a linear increase in %B from 17% to 51%. Absorbance was monitored at 214 nm with a Waters model 441 detector.

For second dimension separation, peptide peaks bearing specific label isolated as were collected at 0° C., stored frozen at −70° C., thawed at 0° C., mixed with an equal volume of 100 mM PO$_4$ pH 2.7, and subjected to HPLC as above, except that buffer A was 0.115% trifluoracetic acid (TFA) in H$_2$O and buffer B was 80% ACN, 20% H$_2$O, 0.1% TFA. Peaks bearing specific radiolabel were identified and isolated.

Sample collection: HPLC effluent was collected at the HPLC detector outflow with a Gilson model 203* fraction collector. Samples (100 to 400 fractions per run) were collected and radioactivity measured by adding five volumes of Aquamix (ICN Radiochemicals) followed by scintillation counting. In other studies, on-line liquid scintillation counting was performed using a B-RAM flow radiation detector (INUS Inc.).

Peptide identification: HPLC-isolated peptide were analyzed by both gas phase Edman sequencing and amino acid analysis at the UCSD protein sequencing facility.

RESULTS

Figure 1B:
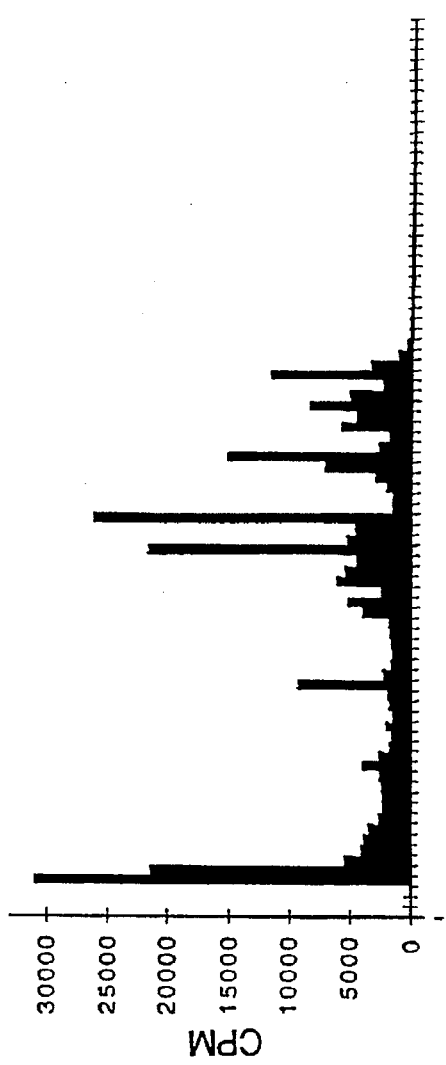

Hemoglobin-monoclonal antibody epitope mapping. Hemoglobin was on-exchanged for 4 hours and then either proteolyzed without a period of off exchange (FIG. 1b), mixed with equimolar quantity of $\beta^6$ monoclonal and then off-exchanged for 40 hours (FIG. 1c), mixed with monoclonal $\beta^{121}$ and off-exchanged for 40 hours (data not shown) or off-exchanged 40 hours in the absence of added antibody (FIG. 1d). When labeled hemoglobin is examined without a period of off exchange (FIG. 1b), at least 17 radiolabeled peaks were resolved, which generally corresponded to the peaks seen in the optical density trace of the same HPLC run (FIG. 1a). When labeled hemoglobin was allowed to fully off exchange without the presence of a protecting monoclonal antibody, all radiolabeled peaks disappeared (FIG. 1d). However, when labeled hemoglobin was off-exchanged in the presence of the $\beta^6$ monoclonal, a single unique peak bearing radiolabel was seen indicating that this fraction contains the $\beta^6$ monoclonal antigenic epitope (FIG. 1c).

Figure 2:
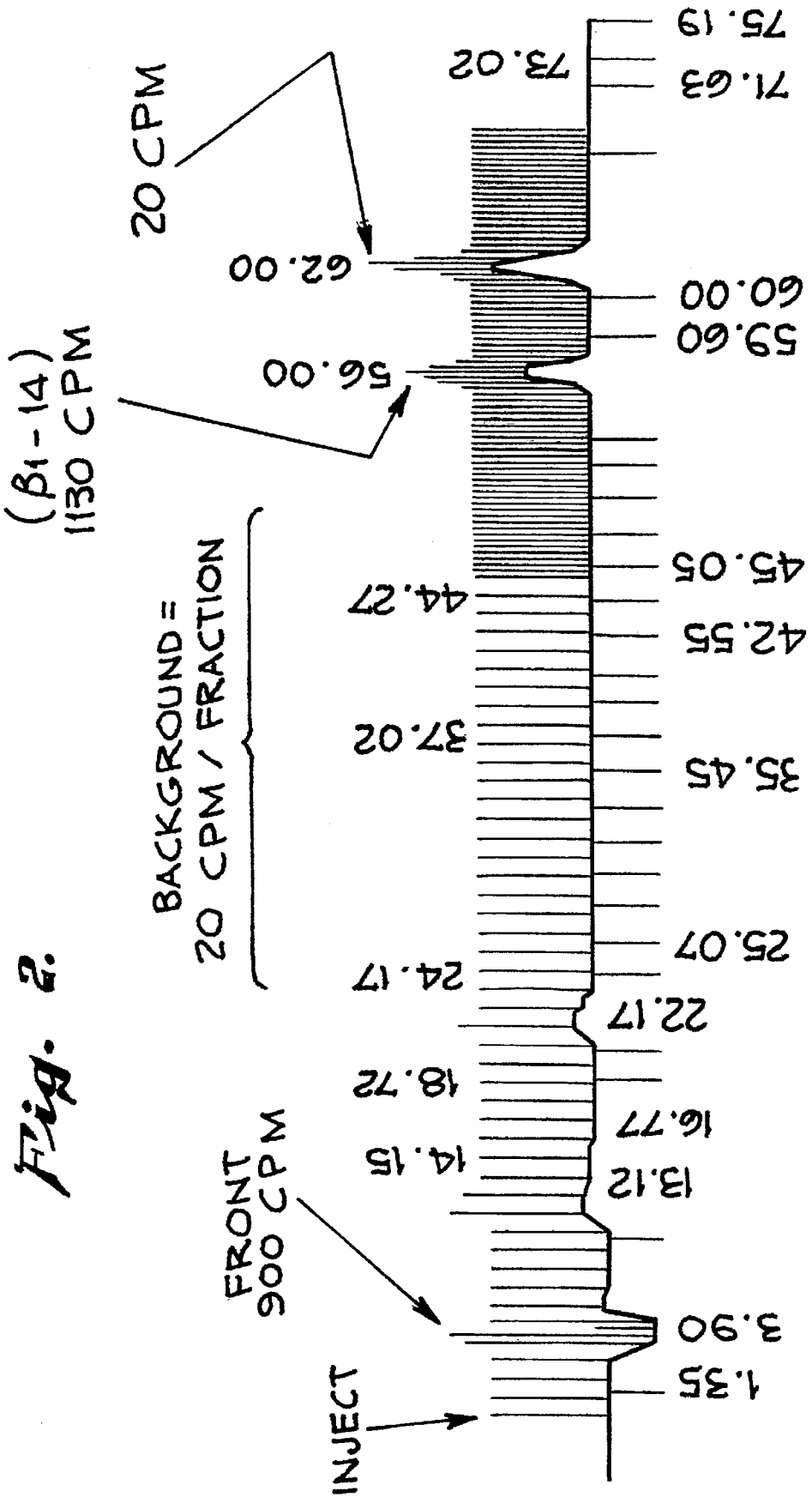
FIG. 2 depicts the results of second dimension separation (HPLC with 0.1% Trifluroracetic Acid (TFA) containing solvents) at 0° C. of tritium-bearing rpHPLC fraction from first dimension separation, FIG. 1, panel C.

When this peak was subjected to second dimension HPLC in TFA-containing solvents under slowed proton exchange conditions, two peptides were resolved by optical density at 214 nM, with only one of these bearing radiolabel (see FIG. 2). This label-bearing peptide was found by gas phase microsequencing and amino acid analysis to represent residues 1–14 of the hemoglobin beta chain. Measurement of on-exchange rates of labeled amides in this peptide demonstrated two rate classes, both of equal size; one which exchanged on with a half life of less than 10 seconds, and another with a half life of approximately 1 hour. Specific activity measurements indicate that 4.3 amide protons within this 14-mer peptide are slowed by interaction of the $\beta^6$ antibody with hemoglobin. A synthetic peptide identical to residues 1–14 of the hemoglobin B chain (B1–14) was synthesized, tritium labeled by proton exchange, and subjected to graded digestion with carboxypeptidase-P (see FIGS. 6a–e).

Figure 3A:
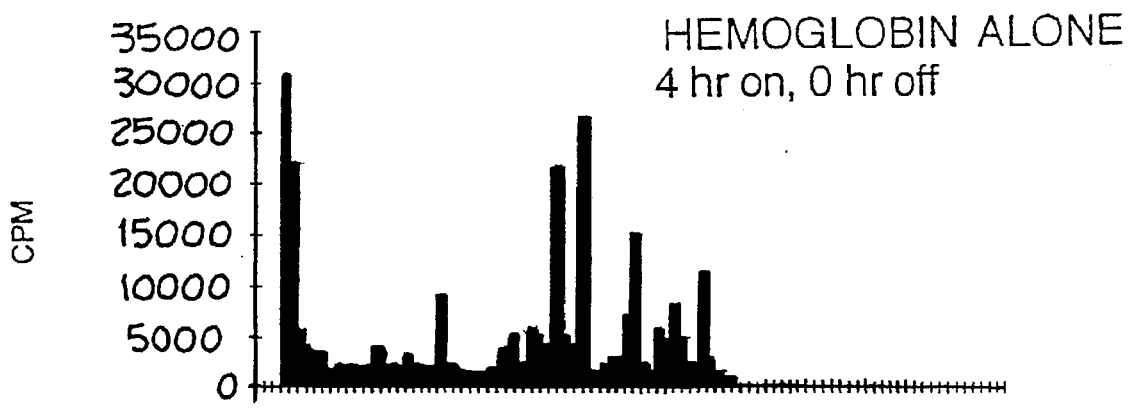
FIGS. 3a–c show the identification (Panels A to C) of hemoglobin peptides functionally labeled by interaction with monoclonal β121.
Figure 3B:
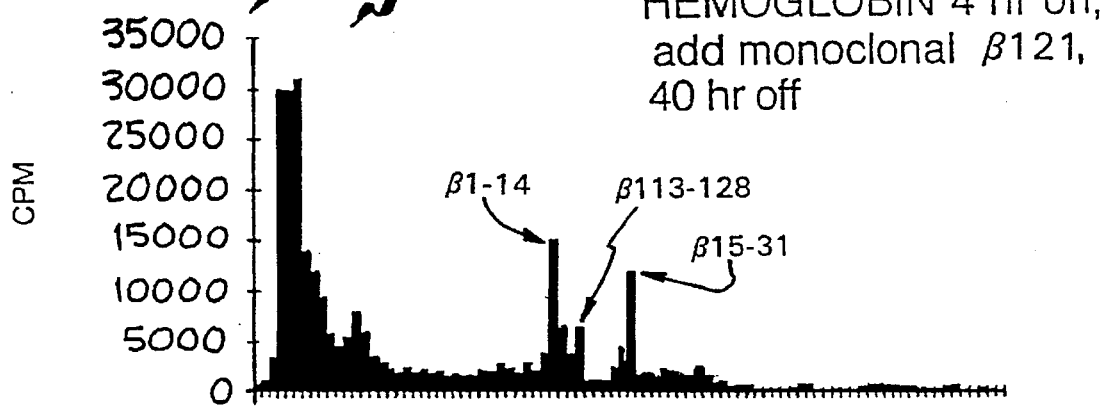
Figure 3C:
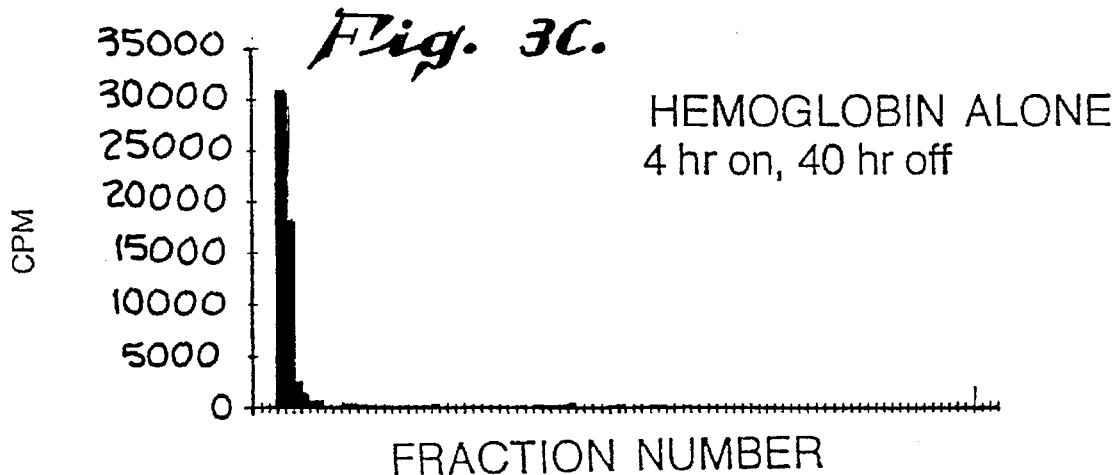

Similar studies were performed with hemoglobin off-exchanged after interaction with β121 monoclonal (FIGS. 3a–c). Three pepsin-generated peptides were found to bear tritium label (FIG. 3b). After second dimension HPLC separation in TFA-containing solvents these peaks were similarly resolved from contaminants, sequenced, and found to be hemoglobin polypeptides β1–14, β113–128, and β15–31. In preliminary proton counting studies, approximately two β121 monoclonal-slowed protons are present in each of these three peptides.

Figure 5A:
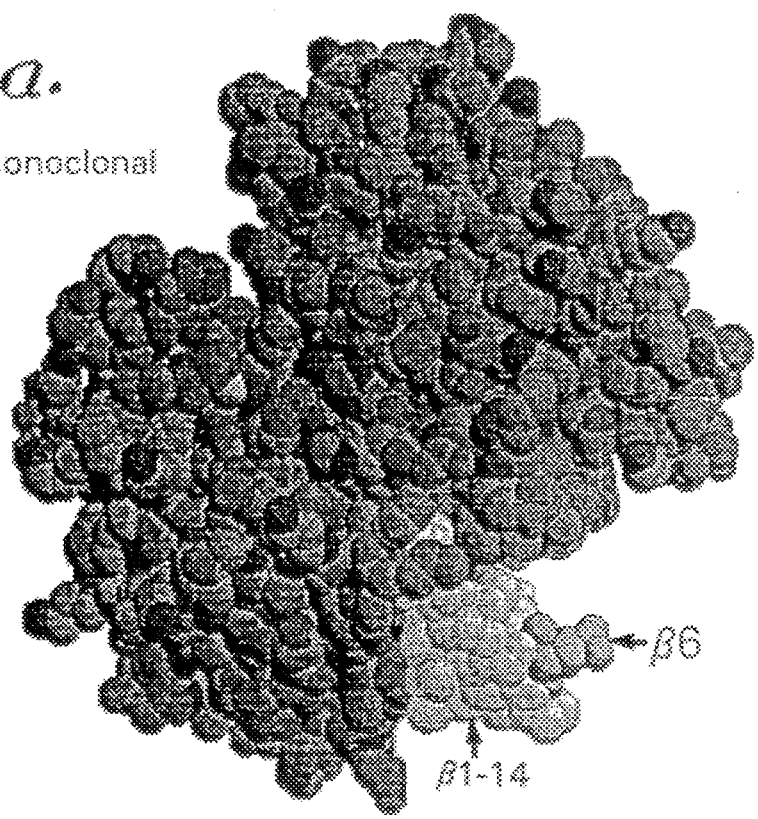
FIG. 5a–b shows the structure of hemoglobin with peptidic regions highlighted.
Figure 5B:
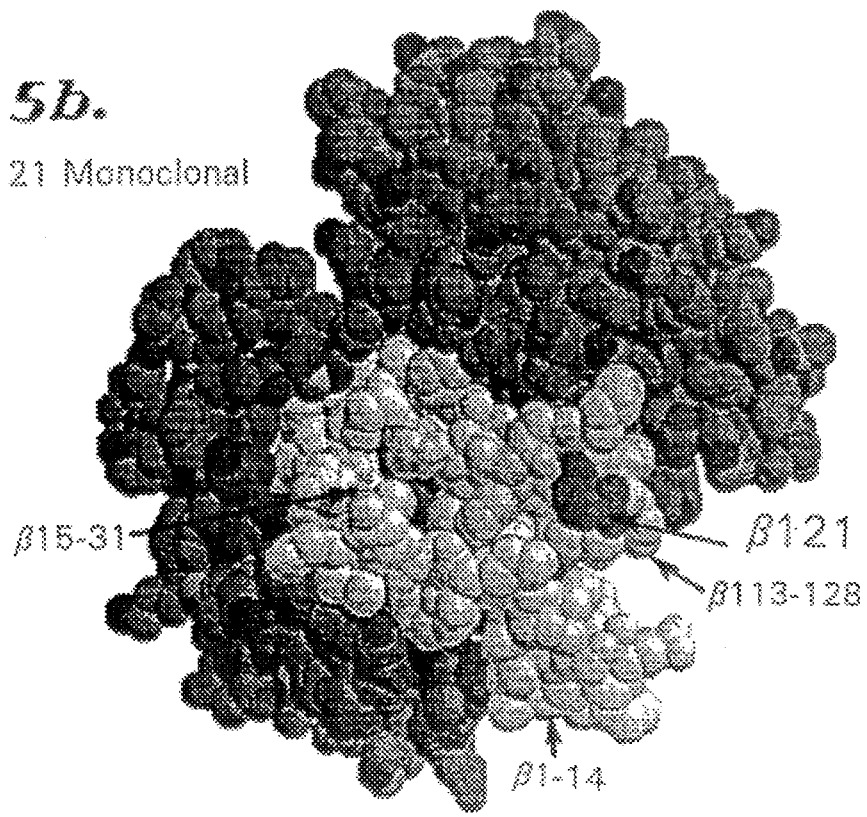

The position of these peptidic regions in the folded hemoglobin tetramer are shown in FIGS. 5a and 5b. The $\beta^6$ monoclonal labels six amide bonds which are present on an externally disposed segment of the folded hemoglobin molecule (β chain amino acids 1–14) which includes the previously characterized target epitope of this monoclonal (β6–9) (51). The $\beta^{121}$ monoclonal labels a total of approximately six protons which, though present on the non-contiguous regions of the linear amino acid sequence of hemoglobin are seen to be surface disposed and located in close proximity to each other in the folded hemoglobin molecule, and include the hemoglobin β chain 121 residue.

Mapping of hemoglobin-haptoglobin interaction sites: When hemoglobin binds to haptoglobin it is known that the hemoglobin molecule contacts haptoglobin through three non-contiguous peptidic regions which consist of hemoglobin α chain 121–127, β11–25 and β131–146 (52,53). We therefore anticipated that pepsin cleavage of hemoglobin labeled at haptoglobin interaction sites would display between 2 and 10 radiolabeled peptides. We therefore performed our haptoglobin studies at a higher level of resolution, accomplished by collection of a larger number of HPLC fractions (see FIGS. 4a–d). Under these conditions, labeled hemoglobin analyzed without a period of off exchange demonstrates greater than 33 discernable radiolabeled peaks (FIG. 4b), which again correspond to the optical density tracing (FIG. 4a). Labeled hemoglobin off-exchanged in the presence of haptoglobin produces 7 specifically radiolabeled peaks (FIG. 4c) which are not present if hemoglobin is off-exchanged in the absence of haptoglobin (FIG. 4d). These results indicate that this technology works well with a receptor-like ligand interaction system as complex as that of hemoglobin with haptoglobin.

Solvent Effect

Synthetic hemoglobin β1–14 peptide was tritium-labeled at all peptide amides by proton exchange, and aliquots of labeled peptide subjected to 0° C. HPLC analysis as in FIG. 1 except that a range of solvent pH's were utilized as indicated below. The percent of original peptide-bound tritium that remained bound to the peptide under each HPLC condition was then determined.

| pH | A solvent | B solvent |
|---|---|---|
| 2.1 | 0.115% TFA in water | 80% ACN, 20% H$_2$O, 0.1% TFA |
| 2.7 | 50 mM PO$_4$, pH 2.7 | 80% ACN, 20% 50 mM PO$_4$, pH 2.7 |
| 3.5 | 50 mM PO$_4$, pH 3.5 | 80% ACN, 20% 50 mM PO$_4$, pH 3.5 |
| 4.0 | 50 mM PO$_4$, pH 4.0 | 80% ACN, 20% 50 mM PO$_4$, pH 4.0 |

Tritium retention was about 57% for TFA (ph 2.1), 46% for PO$_4$ (ph 2.7), 34% for PO$_4$ (ph 3.5), and 14% for PO$_4$ (ph 4.0).

REFERENCES

1. Horsfall, A. C., et al., Epitope mapping. *Immunology Today* 12:211–213, 1991.

2. Arnon, R., et al., Structural basis of antigenic specificity and design of new vaccines. *FASEB J* 6:3265–3274, 1992.

3. Englander, S. W., et al., The assignment of proton resonances in 2D NMR spectra of proteins. *Techniques in Protein Chemistry*, TE Hughim ed. Academic Press, San Diego, pg 207–222, 1989.

4. Englander, S. W., et al., Hydrogen-Tritium exchange. *Methods in Enzymology* 49:24–39, 1978.

5. Englander, S. W., et al., Hydrogen-tritium exchange. *Methods in Enzymology* 26:406–413, 1972.

6. Englander, J. J., et al., Protein hydrogen exchange studied by the fragment separation method. *Analytical Biochemistry* 147:234–244, 1985.

7. Englander, S. W., et al., Hydrogen-tritium exchange of the random chain polypeptide. *Biopolymers* 7:379–393, 1969.

8. Molday, R. S., et al., Primary structure effects on peptide group hydrogen exchange. *Biochemistry* 11:150, 1972.

9. Kim, P. S., et al., Influence of charge on the rate of amide proton exchange. *Biochemistry* 21:1, 1982.

10. Bai, Y., et al., Primary structure effects on peptide group hydrogen exchange. *Proteins: Structure, Function, and Genetics* 17:75–86, 1993.

11. Connelly, G. P., et al., Isotope effects in peptide group hydrogen exchange. *Proteins: Structure, Function, and Genetics* 17:87–92, 1993.

12. Englander, S. W., et al., Hydrogen exchange studies or respiratory proteins. III. Structural and free energy changes in hemoglobin by use of a difference method. *J. Biol. Chem.* 248:4852–4861, 1973.

13. Englander, J. J., Hydrogen-tritium exchange survey of allosteric effects in hemoglobin. *Biochemistry* 26:1846–1850, 1987.

14. Louie, G., et al., Salt, phosphate and the Bohr effect at the haemoglobin beta chain C terminus studied by hydrogen exchange. *J. Mol. Biol.* 201:765–772, 1988.

15. Rosa, J. J., et al., An experimental procedure for increasing the structural resolution of chemical hydrogen-exchange measurements on proteins: Application to ribonuclease S peptide. *J. Mol. Biol.* 133:399–416, 1979.

16. Rosa, J. J., et al., Hydrogen exchange from identified regions of the S-protein component of ribonuclease as a function of temperature, pH, and the binding of S-peptide. *J. Mol. Biol.* 145:835–851, 1981.

17. Rosa, J. J., et al., Effects of binding of S-peptide and 2'-cytidine monophosphate on hydrogen exchange from the protein component of ribonuclease S. *J. Mol. Biol.* 160:517–530, 1982.

18. Englander, S. W., et al., Individual breathing reactions measured in hemoglobin by hydrogen exchange methods. *Biophys. J.* 10:577, 1979.

19. Rogero, J. R., et al., Individual breathing reactions measured by functional labeling and hydrogen exchange methods. *Methods in Enzymology* 131:508–517, 1986.

20. Ray, J., et al., Allosteric sensitivity in hemoglobin at the α-subunit N-terminus studied by hydrogen exchange. *Biochemistry* 25:3000–30007, 1986.

21. Louie, G., et al., Allosteric energy at the hemoglobin beta chain C terminus studied by hydrogen exchange. *J. Mol. Biol.* 201:755–764, 1988.

22. Burz, D. S., et al., Mapping structure perturbation in *escherichia coli* aspartate transcarbamylase by medium resolution hydrogen exchange. *Biophys. J.* 49:70–72, 1986.

23. Mallikarachchi, D., et al., Effects of ATP and CTP on the conformation of the regulatory subunit of *escherichia coli* aspartate transcarbamylase in solution: A medium-resolution hydrogen exchange study. *Biochemistry* 28:5386–5391, 1989.

24. Beasty, A. M., et al., Characterization of an early intermediate in the folding of the α subunit of tryptophan synthase by hydrogen exchange measurement. *Biochemistry* 24:3547–3553, 1985.

25. Fromajeot, et al., U.S. Pat. No. 3,828,102. Method for preparation of tritium labeled proteins. Filed Sep. 19, 1972, issued August 1974.

26. Benson. U.S. Pat. Nos. 3,560,158 and 3,623,840. Method for analysis of labile hydrogen containing compounds. Filed Aug. 12, 1965, issued Feb. 2, 1971.

27. Fesik, et al., *Biochem Biophys Res Comm* 147(3):892–898, 1987.

28. Paterson, Y., et al., An antibody binding site on cytochrome c defined by hydrogen exchange and two-dimensional NMR. *Science* 249:755–759, 1990.

29. Mayne, L., et al., Effect of antibody binding on protein motions studied by hydrogen-exchange labeling and two-dimensional NMR. *Biochemistry* 31:10678–10685, 1992.

30. Benjamin, D. C., et al., Long-range changes in a protein α antigen due to antigen-antibody interaction. *Biochemistry* 31:9539–9545, 1992.

31. Ruegg, Uth, et al., Reductive cleavage of cystine disulfides with tributyl phosphine. *Meth Enzymol* 47:111–117, 1977.

32. Kirley, T. L., Reduction and fluorescent labeling of cyst(e)ine-containing proteins for subsequent structural analyses. *Anal Biochem* 180:231, 1989.

33. Burns, J. A., et al., Selective reduction of disulfides by Tris (2-carboxyethyl) phosphine. *J Org Chem* 56:2648–2650, 1991.

34. Levison, M. E., et al., Reduction of biological substances by water-soluble phosphines: Gamma globulin (IgG). *Experientia* 25:126–127, 1969.

35. Gray, W. R., Disulfide structures of highly bridged peptides: A new strategy for analysis. *Protein Science* 2:1732–1748, 1993.

36. Gray, W. R., Echistatin disulfide bridges: Selective reduction and linkage assignment. *Protein Science* 2:1479–1755, 1993.

37. Takayuki, T., et al., Cathepsin D from porcine and bovine spleen. *Methods in Enzymology* 80:565–581, 1981.

37a. Krishnan, S., et al., Purification of an acid protease and a serine carboxypeptidase from Aspergillus niger using metal-chelate affinity chromatography. *J Chromatography* 329:165–170, 1985.

37b. Xiaoming, L., et al., A novel carboxylesterase from aspergillus niger and its hydrolysis of succinimide esters. *Carlsberg Res Commun* 54:241–249, 1989.

37c. Zhu, H., et al., Purification and characterization of an extracellular acid proteinase from the ectomycorrhizal fungus *Hebeloma crustuliniforme*. *Applied Environmental Microbiology* 56:837–843, 1990.

38. Fusek, M., et al., Enzymic properties of thermopsin. *J Biol Chem* 265:1496–1501, 1990.

39. Breddam, K. Serine carboxypeptidases. A review. *Carlsberg Res Commun* 51:83–128, 1986.

40. Tsugita, A., Developments in protein microsequencing. *Adv Biophys* 23:81–113, 1987.

40a. Byrne, R. H., et al., An improved freeze-drying technique for the study of hydrogen exchange of proteins and polypeptides. *Analytical Biochemistry* 33:414–428, 1970.

40b. Schreier, A. A., et al., Concentration-dependent hydrogen exchange kinetics of $^3$H-labeled S-peptide in ribonuclease S. *J Mol Biol* 105:409–426, 1976.

41. Smith, C. E., et al., Carboxy-terminal protein sequence analysis using carboxypeptidase P and electrospray mass spectrometry. *Techniques in Protein Chemistry IV*, pg 463, 1993.

42. Rosuack, K. J., et al., C-terminal sequencing of peptides using electrospray ionization mass spectrometry. *Rapid Communications in Mass Spectrometry* 6:637–640, 1992.

43. Loo, J. A., et al., Primary sequence information from intact proteins by electrospray ionization tandem mass spectrometry. *Science* 248:201–204, 1990.

44. McCloskey, J. A., Introduction of deuterium by exchange for measurement by mass spectrometry. *Methods in Enzymology* 193:329–338, 1990.

45. Thevenon-Emeric, G., et al., Determination of amide hydrogen exchange rates in peptides by mass spectrometry. *Anal Chem* 64:2456–2458, 1992.

46. Winger, B. E., et al., Probing qualitative conformation differences of multiply protonated gas-phase proteins via H/D isotopic exchange with $D_2O$. *J Am Chem Soc* 114:5897–5989, 1992.

47. Zhang, Z., et al., Determination of amide hydrogen exchange by mass spectrometry: A new tool for protein structure elucidation. *Protein Science* 2:522–531, 1993.

48. Katta, V., et al., Hydrogen/Deuterium exchange electrospray ionization mass spectrometry: A method for probing protein conformational changes in solution. *J Am Chem Soc* 115:6317–6321, 1993.

49. Chi, H. T., et al., Use of deuterium-hydrogen exchange to characterize the fragmentation pathways of arteether and its metabolites in a thermospray mass spectrometer. *Organic Mass Spectrometry* 28:12–17, 1993.

50. Sepetov, N. F., et al., The use of hydrogen-deuterium exchange to facilitate peptide sequencing by electrospray tandem mass spectrometry. *Rapid Communication in Mass Spectrometry* 7:58–62, 1993.

51. Kiefer, C. R. et al., Negative screening for sickle cell diseases with a monoclonal immunoassay on newborn blood eluted from filter paper. *J. Lab. Clin. Med.* 116:826–830, 1990.

52. Yoshioka, N. et al., Haemoglobin binding with haptoglobin. *Biochem. J.* 234:453–456, 1986.

53. McCormick, D. J., et al., Hemoglobin binding with haptoglobin: Delineation of the haptoglobin binding site on the α-chain of human hemoglobin. *J. Protein Chem.* 9:735, 1990.

54. Tsugita, A. et al., Reaction of pentafluoropropionic anhydride vapor on polypeptide as revealed by mass spectrometry. A carboxypeptidase mimetic degradation. *Chemistry Letters* 235–238, 1992.

55. Tsugita, A., et al., Development of novel c-terminal sequencing methods. *Methods in Protein Sequence Analysis*, edited by K Imahori, F Sakiyama, Plenum Press, New York, 1993, pp. 55.

I claim:

1. A method of characterizing the binding site of a binding protein to a binding partner which comprises:

(a) contacting the binding protein with a tritiated solution for an "on-exchange" period sufficient for substantially each of the exposed peptide amide hydrogen atoms of said binding protein to be replaced by tritium;

(b) forming a complex of the binding protein with its binding partner, wherein as a result of the formation of said complex some of said tritium atoms in the binding site of the binding protein become less accessible to solvent;

(c) contacting said complex with an untritiated solution containing hydrogen atoms for an "off-exchange" period sufficient for substantially all of the tritium atoms still exposed to solvent to be replaced by hydrogen atoms, in which at least one tritium atom is retained which, in the absence of said binding partner, would have been still exposed to solvent and thus replaced by a hydrogen atom;

(d) fragmenting the protein to obtain a plurality of fragments, differing in tritium content;

(e) separating and purifying the fragments;

(f) determining which purified fragments are tritiated by radioactivity measurements;

(g) progressively degrading each purified, tritiated fragment to obtain a series of subfragments of progressively smaller size, and determining by radioactivity measurements which subfragments of the fragment are tritiated, thereby localizing the particular amides within each fragment that still contain exchanged tritium and thus further characterizing the binding site of said binding protein;

wherein steps (d)–(g) are performed under slowed hydrogen exchange conditions such that the tritium is substantially retained at peptide amide hydrogen positions of the binding protein.

2. The method of claim 1 wherein said separating step (e) is accomplished at least in part by reverse phase high pressure liquid chromatography.

3. The method of claim 2 in which the separation is performed by two sequential separations under different conditions.

4. The method of claim 3 in which the two sequential separations are performed at two different pHs, each within the range 3.0–2.1.

5. The method of claim 3 in which one separation is at a pH of about 2.1.

6. The method of claim 1 in which the degrading of the fragments in step (g) comprises exposing of the fragments to acid resistant carboxypeptidase.

7. The method of claim 6 in which the acid resistant carboxypeptidase is carboxypeptidase P, Y, W, or C.

8. The method of claim 1 in which the tritiated solution has a specific activity of 10–100 Ci/ml final concentration.

9. The method of claim 1 in which the tritiated solution has a specific activity of 100–1,000 Ci/ml.

10. The method of claim 1 wherein the binding protein has one or more disulfide bonds, and the method further comprises the step of disrupting said disulfide bonds prior to step (d) under conditions in which the tritium is substantially retained at peptide amide hydrogens of the binding protein.

11. The method of claim 10 wherein disrupting the disulfide bonds is done by reaction with a water soluble phosphine.

12. The method of claim 1 in which progressively degrading the fragment of step (g) is performed at the carboxy-terminal through the use of pentafluoropropionic acid anhydride.

13. The method of claim 1 in which the radioactivity of the peptide fragments after steps (a)–(e) is compared to the radioactivity of the corresponding fragments after the same steps but with step (b) omitted.

14. The method of claim 1 wherein the complex of step (b) is digested to cleave off a portion of the binding protein without dissociating the complex or causing a substantial loss of tritiura from the remainder of the binding protein.

15. A method of characterizing the binding site of a binding protein to a binding partner which comprises:

(a) contacting the binding protein with a deuterated solution for an "on-exchange" period sufficient for substantially each of the exposed peptide amide hydrogen atoms of said binding protein to be replaced by deuterium;

(b) forming a complex of the binding protein with its binding partner, wherein as a result of the formation of said complex some of said deuterium atoms in the binding site of the binding protein become less accessible to solvent;

(c) contacting said complex with an undeuterated solution containing hydrogen atoms for an "off-exchange" period sufficient for substantially all of the deuterium atoms still exposed to solvent to be replaced by hydrogen atoms, in which at least one deuterium atom is retained which, in the absence of said binding partner, would have been still exposed to solvent and thus replaced by a hydrogen atom;

(d) fragmenting the protein to obtain a plurality of fragments, differing in deuterium content;

(e) separating and purifying the fragments;

(f) determining which purified fragments are deuterated by mass spectrometry;

(g) progressively degrading each purified, deuterated fragment to obtain a series of subfragments of progressively smaller size, and determining by mass spectrometry which subfragments of the fragment are deuterated, thereby localizing the particular amides within each fragment that still contain exchanged deuterium and thus further characterizing the binding site of said binding protein;

wherein steps (d)–(g) are performed under slowed hydrogen exchange conditions such that the deuterium is substantially retained at peptide amide hydrogen positions of the binding protein.

* * * * *